(12) United States Patent
Rockweiler et al.

(10) Patent No.: US 9,878,164 B2
(45) Date of Patent: Jan. 30, 2018

(54) CARDIAC PACING WITH ANODAL STIMULATION DETECTION

(71) Applicant: Cardiac Pacemakers, Inc., St. Paul, MN (US)

(72) Inventors: Holly E. Rockweiler, Palo Alto, CA (US); Shibaji Shome, Arden Hills, MN (US); Arjun D. Sharma, St. Paul, MN (US); Deepa Mahajan, Roseville, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 106 days.

(21) Appl. No.: 14/505,136

(22) Filed: Oct. 2, 2014

(65) Prior Publication Data
US 2015/0100103 A1   Apr. 9, 2015

Related U.S. Application Data

(60) Provisional application No. 61/886,893, filed on Oct. 4, 2013.

(51) Int. Cl.
*A61N 1/37* (2006.01)
*A61N 1/368* (2006.01)

(52) U.S. Cl.
CPC .......... *A61N 1/371* (2013.01); *A61N 1/3684* (2013.01); *A61N 1/3686* (2013.01)

(58) Field of Classification Search
None
See application file for complete search history.

(56) References Cited

U.S. PATENT DOCUMENTS

| | | |
|---|---|---|
| 6,687,545 B1 | 2/2004 | Lu |
| 7,711,424 B2 | 5/2010 | Meyer et al. |
| 8,369,963 B2 | 2/2013 | Parramon et al. |
| 8,380,307 B2 | 2/2013 | Lian et al. |
| 8,401,639 B2 | 3/2013 | McCabe et al. |
| 8,565,879 B2 | 10/2013 | Brisben et al. |
| 8,626,291 B2 | 1/2014 | Stadler et al. |
| 8,825,155 B2 | 9/2014 | Zhu et al. |
| 8,825,159 B2 | 9/2014 | Zhu et al. |
| 2009/0030470 A1 | 1/2009 | Holmstrom et al. |

(Continued)

*Primary Examiner* — Erica Lee
(74) *Attorney, Agent, or Firm* — Schwegman Lundberg & Woessner, P.A.

(57) ABSTRACT

Methods and device for determining a pacing vector for delivering an electrostimulation therapy are described. An implantable medical device may be configured to determine an anode capture threshold and a cathode capture threshold for a first anode and cathode pair of electrodes, switch a polarity of the first anode and cathode pair of electrodes, and determine an anode capture threshold and a cathode capture threshold for the first anode and cathode pair of electrodes having the switched polarity. The implantable medical device may be further configured to compare a cathodal capture threshold for the anode and cathode pair having the switched polarity to the anodal capture threshold of the first anode and cathode pair of electrodes and select either an anode or a cathode for delivering an electrostimulation therapy based at least in part on the comparison. Other methods and systems are also contemplated and described.

8 Claims, 15 Drawing Sheets

(56) References Cited

U.S. PATENT DOCUMENTS

| | | | |
|---|---|---|---|
| 2010/0121404 A1* | 5/2010 | Bjorling | A61N 1/3712 607/28 |
| 2011/0145890 A1 | 10/2011 | Brisben et al. | |
| 2012/0130442 A1* | 5/2012 | Rockweiler | A61N 1/3712 607/18 |
| 2013/0030492 A1* | 1/2013 | Stadler | A61N 1/3712 607/28 |
| 2014/0005742 A1 | 1/2014 | Mahajan et al. | |
| 2014/0350623 A1* | 11/2014 | Fischer | A61N 1/3962 607/11 |

* cited by examiner

CARDIAC PACING WITH ANODAL STIMULATION DETECTION

CROSS REFERENCE TO RELATED APPLICATION

This application claims the benefit of U.S. Provisional Application No. 61/886,893, filed Oct. 4, 2013, which application is related to co-pending U.S. Published Application No. 2012/0130442, filed on Nov. 21, 2011, entitled "CARDIAC ANODAL STIMULATION DETECTION", the entire disclosures of which are all incorporated herein by reference.

TECHNICAL FIELD

This application relates to cardiac implantable medical devices and more particularly, to cardiac implantable medical devices and methods to discriminate between anodal stimulation and cathodal stimulation to aid in determining an appropriate pacing vector.

BACKGROUND

Electrostimulation can be delivered to a heart, such as to trigger or to spatially coordinate a responsive cardiac depolarization and accompanying heart contraction. An implantable or other ambulatory cardiac function management device, such as a pacer, a cardioverter, a defibrillator, a cardiac contractility modulation (CCM) or a cardiac resynchronization therapy (CRT) device can be configured to include capability for monitoring cardiovascular function or for generating or providing such stimulation to the heart, such as for triggering or spatially coordinating responsive heart contractions. Such electrostimulations can be delivered via two or more electrodes. For example, such electrodes can include one or more electrodes that can be located at or near the distal end of one or more implantable leadwires, which can be connected to an implantable cardiac function management device. Such electrodes can also include one or more electrodes located at the implantable cardiac function management device.

Electrostimulation can be either cathodal or anodal, or a combination of anodal and cathodal. In cathodal stimulation, a more negative electrode (e.g., in an arrangement of electrodes) "captures" contractile cardiac tissue to trigger the resulting cardiac depolarization and accompanying heart contraction. In anodal stimulation, a more positive electrode (e.g., in an arrangement of electrodes) triggers the resulting cardiac depolarization and accompanying heart contraction. Various factors can influence whether anodal or cathodal stimulation occurs. For example, relative electrode size of an anode vs. a cathode can determine whether anodal, cathodal, or a combination of anodal and cathodal stimulation occurs. An electrode having a smaller surface area can have a greater current density through nearby tissue than a larger electrode. Greater current density can lower the threshold amount of energy needed to evoke a resulting cardiac depolarization and accompanying heart contraction.

The threshold amount of energy needed to evoke a resulting cardiac depolarization and accompanying heart contraction can differ for anodal stimulation vs. cathodal stimulation. Typically, for a selected electrode, the anodal stimulation threshold is higher than the electrode's cathodal stimulation threshold. Discriminating between anodal stimulation and cathodal stimulation during the delivery of an electrostimulation therapy may be useful in determining an optimal pacing configuration. For example, in some cases, it may be that the anodal threshold is lower than the cathodal electrode for a particular electrode site.

SUMMARY

The present disclosure relates generally to cardiac implantable medical devices and more particularly, to cardiac implantable medical devices and methods used to discriminate between anodal stimulation and cathodal stimulation to aid in determining an appropriate pacing vector. For example, in one illustrative embodiment, an implantable medical device includes: an electrostimulation energy delivery circuit configured to deliver a number of pacing pulses to a subject's heart via an electrode configuration comprising a first electrode and a second electrode; an evoked response (ER) sensing circuit configured to sense an ER signal of a subject in response to each of the delivered pacing pulses; and a processor circuit, coupled to the ER sensing circuit and the electrostimulation energy delivery circuit. In some cases, in an operating mode of the device, the processor circuit can be configured to: cause the electrostimulation energy delivery circuit to deliver a number of pacing pulses using a first polarity of the first electrode and the second electrode; cause the electrostimulation energy delivery circuit to adjust a pacing energy of the delivered pacing pulses over time, and monitor the ER signal via the evoked response (ER) sensing circuit until a change is detected that indicates a change in capture at the first electrode and/or at the second electrode; and once a change is detected that indicates a change in capture at the first electrode and/or the second electrode, identify from the evoked response if capture is occurring at the second electrode but not the first electrode, and if so, cause the electrostimulation energy delivery circuit to switch the polarity of the first electrode and the second electrode to a second polarity, and if not, maintain the first polarity of the first electrode and the second electrode.

In another illustrative embodiment, a method of determining a pacing configuration can include: delivering a number of pacing pulses to a subject's heart via an electrostimulation energy delivery circuit using a first polarity of a first electrode and a second electrode; adjusting a pacing energy of the delivered pacing pulses over time via the electrostimulation energy delivery circuit; and monitoring an ER signal via an evoked response (ER) sensing circuit until a change is detected that indicates a change in capture at the first electrode and/or the second electrode. In some cases, once a change is detected that indicates a change in capture at the first electrode and/or the second electrode, a processing circuit identifying from the evoked response if capture is occurring at the second electrode but not at the first electrode, and if so, causing the electrostimulation energy delivery circuit to switch the polarity of the first electrode and the second electrode to a second polarity, and if not, maintaining the first polarity of the first electrode and the second electrode.

In another illustrative embodiment, a computer readable medium may store, in a non-transitory state, a set of instructions that cause an implantable medical device to: deliver a number of pacing pulses to a subject's heart using a first polarity of a first electrode and a second electrode; adjust a pacing energy of the delivered pacing pulses over time; monitor an Evoked Response (ER) to each of the pacing pulses until a change is detected that indicates a change in capture at the first electrode and/or the second electrode; and, once a change is detected that indicates a change in capture at the first electrode and/or the second electrode, identify from the ER if capture is occurring at the second electrode but not at the first electrode, and if so, switch the polarity of the first electrode and the second electrode to a second polarity, and if not, maintaining the first polarity of the first electrode and the second electrode.

In another illustrative embodiment, an implantable medical device can include: an electrostimulation energy delivery circuit comprising a plurality of electrodes; and a processor circuit coupled to the electrostimulation energy delivery circuit. In some cases, the processor circuit can be configured to: determine an anode capture threshold and a cathode capture threshold for a first anode and cathode pair of electrodes, with a first electrode as the cathode and a second electrode as the anode; determine an anode capture threshold and a cathode capture threshold for a second anode and cathode pair of electrodes, with a third electrode as the cathode and a fourth electrode as the anode; determine which electrode has the lowest capture threshold; select the first electrode as the cathode electrode if the first electrode has the lowest capture threshold; select the third electrode as the cathode electrode if the third electrode has the lowest capture threshold; and cause subsequent pacing pulses to be delivered via the electrostimulation energy delivery circuit using the selected cathode electrode and a selected anode electrode.

In yet another illustrative embodiment, an implantable medical device can include: an electrostimulation energy delivery circuit comprising a plurality of electrodes; and a processor circuit coupled to the electrostimulation energy delivery circuit. In some cases, the processor circuit can be configured to: determine an anode capture threshold and a cathode capture threshold for at least a first anode and cathode pair of electrodes; determine which capture threshold of the first anode and cathode pair and the second anode and cathode pair has a lowest capture threshold energy; switch a polarity of the anode and cathode pair having the lowest capture threshold energy; and compare a cathodal capture threshold for the anode and cathode pair having the switched polarity to the anodal capture threshold of the first anode and cathode pair and the second anode and cathode pair and select either an anode or a cathode for delivering an electrostimulation therapy based at least in part on the comparison.

In yet another illustrative embodiment, a method of determining a pacing configuration can include: delivering a pacing pulse to a subject's heart via an electrostimulation energy delivery circuit comprising a plurality of electrodes; determining an anode capture threshold and a cathode capture threshold for a first anode and cathode pair of electrodes at a processor coupled to the electrostimulation energy delivery circuit; switching a polarity of the first anode and cathode pair of electrodes; and determining an anode capture threshold and a cathode capture threshold for the first anode and cathode pair of electrodes having the switched polarity. Additionally, the method can further include comparing a cathodal capture threshold for the anode and cathode pair having the switched polarity to the anodal capture threshold of the first anode and cathode pair of electrodes determined prior to the switch in polarity; and the processor selecting either an anode or a cathode for delivering an electrostimulation therapy based at least in part on the comparison.

In yet another illustrative embodiment, a method of determining an electrode configuration for delivering an electrostimulation therapy to a patient's heart can include: a) delivering a pacing pulse to a patient's heart at a sufficient pacing output energy level to cause both anodal and cathodal capture via an electrostimulation energy delivery circuit comprising at least a first anode and cathode pair of electrodes; b) changing the pacing output energy level in accordance with a capture threshold test for a first anode and cathode pair of electrodes; c) determining at a processor coupled to the electrostimulation energy delivery circuit which electrode of the first anode and cathode pair of electrodes loses capture first; d) selecting a second anode and cathode pair of electrode for continuing capture threshold testing, wherein at least one electrode of the second anode and cathode electrode pair is selected from the first anode and cathode pair based on the determination of which of the anode or the cathode loses capture first; e) continuing the capture threshold testing using the second anode and cathode pair of electrodes; and f) comparing a cathode capture threshold of the first anode and cathode pair to the cathode capture threshold of the second anode cathode pair and selecting a cathode for delivering an electrostimulation therapy based, at least in part, on the comparison.

In still yet another illustrative embodiment, an implantable medical device can include: an electrostimulation energy delivery circuit comprising a plurality of electrodes configured to deliver a pacing pulse to a subject's heart; an evoked response (ER) sensing circuit, configured to sense an ER signal of a subject in response to a delivered pacing pulse; and a processor circuit, coupled to the ER sensing circuit and the electrostimulation energy delivery circuit. In some cases, the processor circuit can be configured to initiate a capture threshold test for a first anode and cathode pair of electrodes, determine which of the anode or the cathode loses capture first, and to select a second anode and cathode electrode pair from the plurality of the electrodes to continue the capture threshold test, wherein at least one electrode of the second anode and cathode electrode pair is selected from the first anode and cathode pair based on the determination of which of the anode or the cathode loses capture first.

In still yet another illustrative embodiment, a method of determining an electrode configuration for delivering an electrostimulation therapy to a patient's heart can include: a) delivering a pacing pulse to a patient's heart at a sufficient pacing output energy level to cause both anodal and cathodal capture via an electrostimulation energy delivery circuit comprising at least a first anode and cathode pair of electrodes; b) changing the pacing output energy level in accordance with a capture threshold test for a first anode and cathode pair of electrodes; c) determining at a processor coupled to the electrostimulation energy delivery circuit which electrode of the first anode and cathode pair of electrodes loses capture first; d) selecting a second anode and cathode pair of electrode for continuing capture threshold testing, wherein at least one electrode of the second anode and cathode electrode pair is selected from the first anode and cathode pair based on the determination of which of the anode or the cathode loses capture first; e) continuing the capture threshold testing using the second anode and cathode pair of electrodes; and f) comparing a cathode capture threshold of the first anode and cathode pair to the cathode capture threshold of the second anode cathode pair and selecting a cathode for delivering an electrostimulation therapy based, at least in part, on the comparison.

In yet still another illustrative embodiment, a method of determining a stability of a lead's position within a patient's heart can include: delivering a number of pacing pulses to the patient's heart via one or more electrodes located on an electrostimulation lead in accordance with a capture threshold test; repeating the capture threshold testing to determine a plurality of capture threshold measurements for each electrode; calculating a standard deviation of the capture threshold measurements for each electrode; and determining a stability of the lead's position based, at least in part, on the standard deviation of the capture threshold measurements for each electrode The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments in connection with the accompanying drawings, in which.

Figure 1:
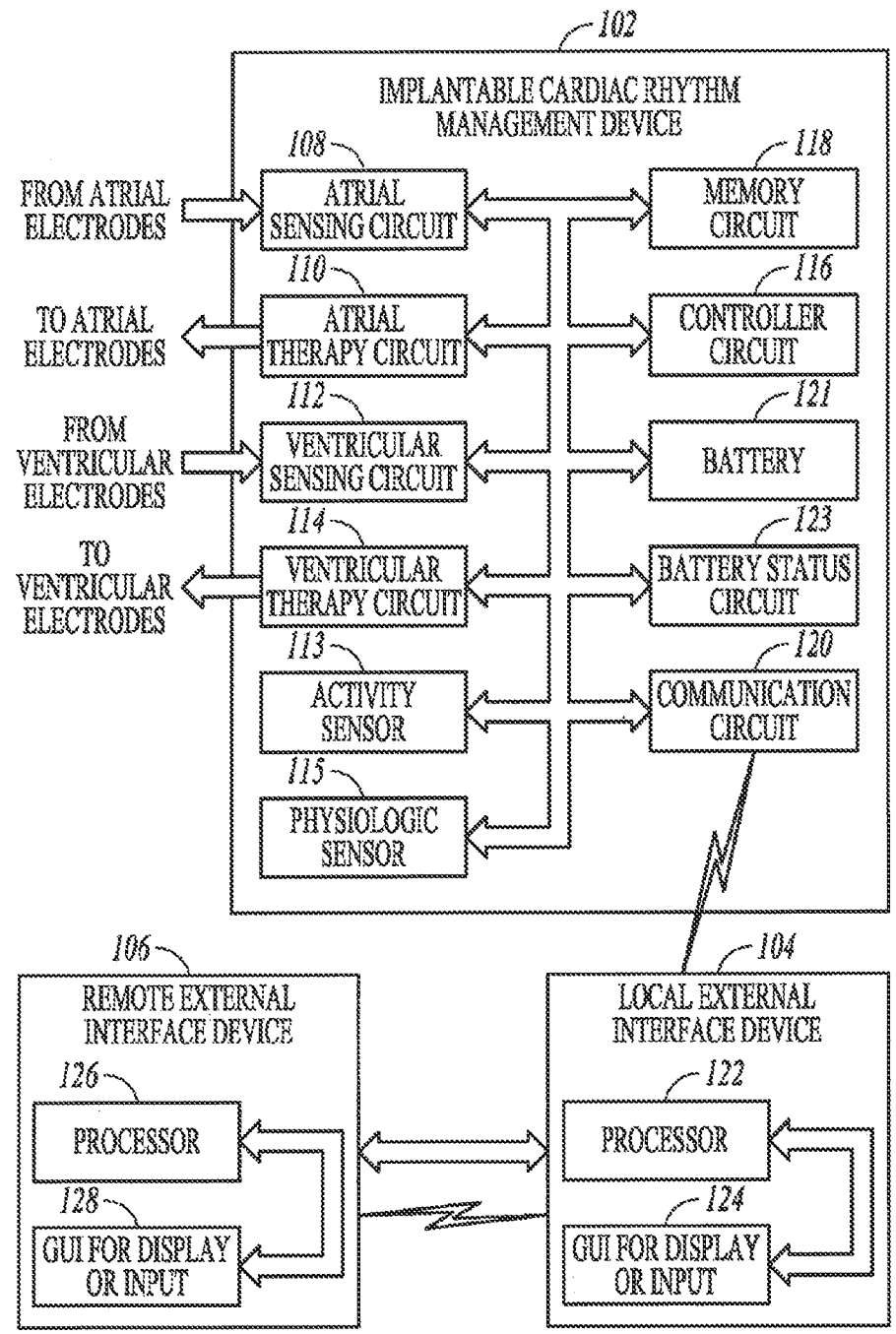
FIG. 1 shows an example of portions of a cardiac function management system and an environment in which it is used.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings wherein like reference numerals indicate like elements throughout the several views. The description and drawings show several embodiments which are meant to illustrative in nature.

FIG. 1 shows an example of portions of a cardiac function management system 100 and an environment in which it is used. In an example, the system 100 can include an ambulatory medical device, such as an external (e.g., wearable) medical device or an implantable cardiac rhythm or function management device 102 for monitoring physiological function or delivering therapy, a local external interface device 104, and an optional remote external interface device 106.

In one example, the implantable device 102 can include an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, a battery status circuit 123, an activity sensor 113 configured to sense a physical activity signal of a patient or other subject, and a physiologic sensor 115 configured to sense a physiologic signal, different from the physical activity signal, of the subject.

The atrial sensing circuit 108 can be coupled to one or more electrodes, such as an intra-atrial electrode or any other electrode that permits sensing of an intrinsic atrial cardiac signal including atrial depolarization information. The atrial therapy circuit 110 can similarly be coupled to these or other electrodes, such as for delivering pacing, cardiac resynchronization therapy (CRT), cardiac contractility modulation (CCM) therapy, defibrillation cardioversion shocks, or other energy pulses to one or both atria. In some cases, the atrial sensing circuit 108 or the atrial therapy circuit 110 can be multiplexed or replicated, such as to interface with both a right atrium and a left atrium.

The ventricular sensing circuit 112 also can be coupled to one or more electrodes, such as an intra-ventricular electrode or any other electrode that permits sensing of an intrinsic ventricular cardiac signal including ventricular depolarization information. The ventricular therapy circuit 114 can similarly be coupled to these or other electrodes, such as for delivering pacing, cardiac resynchronization therapy (CRT), cardiac contractility modulation (CCM) therapy, defibrillation cardioversion shocks, or other energy pulses to one or both ventricles. In some cases, the ventricular sensing circuit 112 or the ventricular therapy circuit 114 can be multiplexed or replicated, such as to interface with both a right ventricle and a left ventricle.

The activity sensor 113 can include a single or multiple axis accelerometer, such as to sense an acceleration of the subject that is indicative of physical activity of the subject. The activity sensor 113 can also include a sensor interface circuit, configured to process the acceleration signal and provide a resulting physical activity signal. In one example, the physical activity signal can be indicative of a physical exertion of the subject. In some cases, the activity sensor 113 can also be used for one or more other purposes, such as to sense the subject's posture, heart-sounds, or other information available from an acceleration signal.

In some cases, the physiologic sensor 115 can include a respiration sensor, such as an impedance or other sensor, which can include electrodes configured to deliver a test energy, such as to the subject's thorax, and to sense a responsive voltage signal, such as indicative of the thoracic impedance, and which can be filtered to provide information about respiration (e.g., minute ventilation), heart contraction, or thoracic fluid accumulation.

A controller circuit 116 can be coupled to the atrial sensing circuit 108 and the ventricular sensing circuit 112, such as to receive information from the sensed cardiac signals. The controller circuit 116 can also be coupled to the activity sensor 113 to receive information about the subject's physical activity or exertion level. The controller circuit 116 can also be coupled to the physiologic sensor 115, such as to receive other physiologic information. In an example, such other physiologic information can include cardiac contraction signal, such as to provide information about the subject's heart rate or interval, stroke volume, or other information available from the cardiac contraction signal. In an example, the other physiologic information can include a respiration signal, such as to provide information about the subject's breathing rate or interval, tidal volume, or other information available from the respiration signal. In an example, the controller circuit 116 can include a signal processor circuit, such as a digital signal processor (DSP) circuit.

In some cases, the controller circuit 116 can be coupled to the atrial therapy circuit 110 and the ventricular therapy circuit 114 such as to provide control or triggering signals to trigger timed delivery of the therapy pulses. In an example, the controller circuit 116 can be configured to provide control to help permit the therapy to be effectively delivered, such as in combination with one or more other therapies (e.g., bradycardia pacing, antitachyarrhythmia pacing (ATP), cardiac contractility modulation (CCM) therapy, cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.). In an example, this can include providing dedicated modules within the controller circuit 116, or providing executable, interpretable, or otherwise performable code on a tangible machine-readable medium to configure the controller circuit 116.

A memory circuit 118 can be coupled to the controller circuit 116, such as to store control parameter values, physiological data, performable code or instructions, or other information. A communication circuit 120 can be coupled to the controller circuit 116 such as to permit radiofrequency (RF) or other wireless communication with an external device, such as the local external interface device 104 or the remote external interface device 106.

The battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

The local external interface device 104 can include a processor 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 can include a processor 126 and a graphic user interface (GUI) 128 or like device for displaying information or receiving user input as well as a communication circuit, such as to permit wired or wireless communication with the local external interface device 104 over the communications or computer network.

Because the system 100 includes processing capability in the ambulatory or implantable device 102 (e.g., provided by the controller circuit 116), the local external interface device 104 (e.g., provided by the processor 122), and the remote external interface device 106 (e.g., provided by the processor 126), various functions or methods discussed in this document can be implemented at any of such locations, or tasks of such functions or methods can be distributed between two or more of such locations.

Figure 2:
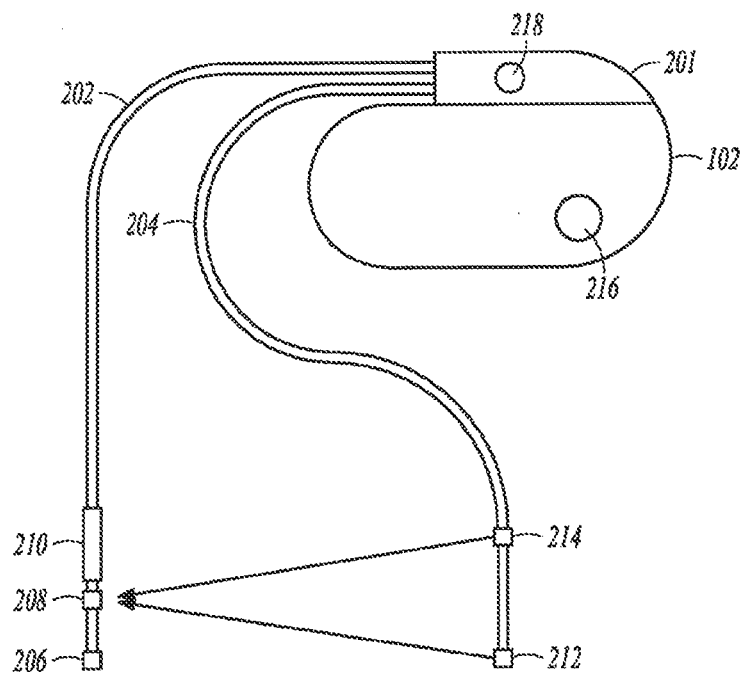
FIG. 2 shows an example of the implantable device connected at a header portion driving a right ventricular (RV) intravascular leadwire and a left ventricular/coronary sinus (LV/CS) intravascular leadwire, such as for use in an "extended bipolar" pacing configuration.

FIG. 2 shows an example of the implantable device 102 connected at a header portion 201 to a right ventricular (RV) intravascular leadwire 202 and a left ventricular/coronary sinus (LV/CS) intravascular leadwire 204. In an example, the RV leadwire 202 can include one or more of an RV tip electrode 206, an RV ring electrode 208, an RV coil electrode 210, or an RA/superior vena cava (SVC) coil electrode. In some cases, such electrodes can be separately addressable, for example, the RV ring electrode 208 can be separately addressable from the RV coil electrode 210, such as to provide a "dedicated bipolar" pacing or sensing electrode configuration using the RV ring electrode 208 and the RV tip electrode 206. In another example, the RV ring electrode 208 and the RV tip electrode 206 can be provided without the RV coil electrode 210 and the RA/SVC coil electrode. In some cases, the LV/CS leadwire 204 can include one or more of an LV tip electrode 212 and LV ring electrode 214. Additionally, in some cases, the implantable device 102 can include an electrode, such as a "can" electrode 216 located on a conductive portion of a can-like hermetically-sealed housing of the electronics unit of the implantable device 102, or a "header" electrode 218 located on a conductive portion located on an insulating "header" extending from the housing of the electronics unit of the implantable device 102.

FIG. 2 illustrates an example of an "extended bipolar" pacing configuration, in which pacing pulses can be delivered between the LV ring electrode 214 and the RV ring electrode 208, or between the LV tip electrode 212 and the RV ring electrode 208. A potential consequence of such an extended bipolar pacing configuration can be cross-chamber anodal capture, such as which can occur when the anode electrode (e.g., RV ring electrode 208) has a small surface area, leading to a large current density near the anode. Such cross-chamber anodal capture can be unintentional or intentional.

When unintended, anodal capture can be difficult for a clinician to recognize in real-time, and can lead to a clinician inappropriately programming the implantable device 102.

For example, during an automatic threshold test, a pacing energy can be lowered (e.g., by decreasing the pacing amplitude or pulse width) until loss of capture (LOC) is detected, such as by a change in morphology of an evoked-response (ER) intrinsic heart signal obtained during a time period after the pacing energy pulse is delivered. However, in an example in which the larger-energy pulses resulted in anodal capture at the RV ring electrode 208, a change in morphology of the evoked response signal can occur due to a loss of anodal capture at the RV ring electrode 208 (e.g., a shift from anodal and cathodal capture to cathodal-only capture), rather than due to a complete loss of capture. If a shift from anodal and cathodal capture to cathodal-only capture is inappropriately deemed a complete loss of capture by an automatic threshold measurement schema, then later pacing can be delivered in excess of a too-large determined pacing threshold voltage. This can shorten the useful life of the implantable device 102, such as where the implantable device 102 is powered by a non-rechargeable battery. As another example of a possible consequence of unintended cross-chamber anodal capture, such as in the extended bipolar pacing configuration of FIG. 2, an unintended negation of interventricular delay can result. For example, a clinician may intend to use the extended bipolar electrode configuration of FIG. 2 to deliver individual RV and LV paces that are separated by a non-zero interventricular delay between such RV and LV paces. Such an interventricular delay can be referred to as a left ventricular (LV) offset. In an example, the clinician may want to issue an LV pace (e.g., between the LV ring electrode 214 and the RV ring electrode 208) slightly before issuing an RV pace (e.g., between the RV tip electrode 206 and the RV ring electrode 208). Such a non-zero time between the issued LV pace and the issued RV pace can be useful, such as where the left ventricular heart contraction is typically abnormally slower than or delayed from the right ventricular heart contraction, which can lead to inefficient blood pumping by the heart. By issuing an LV pace slightly before the RV pace, the left ventricular contraction can be coordinated with the right ventricular contraction, such that both the left and right ventricles contract more concurrently than would be the case without issuing such paces with a non-zero interventricular delay. However, if anodal capture occurs in the right ventricle (such as at the RV ring electrode 208) during an LV pace (e.g., between the LV ring electrode 214 and the RV ring electrode 208), then both right and left ventricles will be paced simultaneously, rather than with the intended non-zero delay between the LV pace pulse followed by the RV pace pulse (the later RV pace pulse may be ineffective, since the right ventricle is already contracting due to the anodal capture occurring with the earlier LV pace pulse). In such an example, the intended cardiac resynchronization providing spatial coordination between the right and left ventricles is absent, and the resulting slower contraction of the left ventricle than that of the right ventricle can result in compromised hemodynamics, such as less efficient pumping of blood than would be obtainable if the left and right ventricular contractions had been properly coordinated as intended. Moreover, it is believed that excessive right ventricular pacing can, over time, sometimes worsen a patient's congestive heart failure status. Delivery of an unintended RV pace pulse, such as that resulting in anodal capture or the later RV bipolar pace pulse rendered ineffective by the earlier anodal capture, can be undesirable.

By contrast, in certain examples, anodal capture may be desirable. For example, in certain patients, zero delay between the LV pace pulse and the RV pace pulse can be desirable in spatially coordinating the left and right ventricles to contract together to promote more efficient pumping of blood. In an extended bipolar pacing example in which a pacing pulse is delivered between the RV ring electrode 208 and one of the LV ring electrode 214 and the LV tip electrode 212, if anodal capture occurs at the RV ring electrode 208 simultaneous with cathodal capture at one of the LV ring electrode 214 and the LV tip electrode 212, then bi-ventricular pacing can be provided via a single pace pulse that locally captures each ventricle, which can provide an energy-efficient way to perform bi-ventricular pacing or cardiac resynchronization. Similarly, in an extended bipolar pacing example in which a pacing pulse is delivered between the RV ring electrode 208 and both of the LV ring electrode 214 and the LV tip electrode 212, if anodal capture occurs at the RV ring electrode 208 simultaneous with cathodal capture at both of the LV ring electrode 214 and the LV tip electrode 212, then "triple site" bi-ventricular pacing can be provided via a single pace pulse that locally captures each ventricle at three different locations, which can resynchronize the heart by concurrently pacing at three different pacing sites, which can be advantageous for certain patients. In another example, "double site" pacing can be obtained, such as with anodal and cathodal capture occurring in the same heart chamber, for example, such as the RV.

Figure 3:
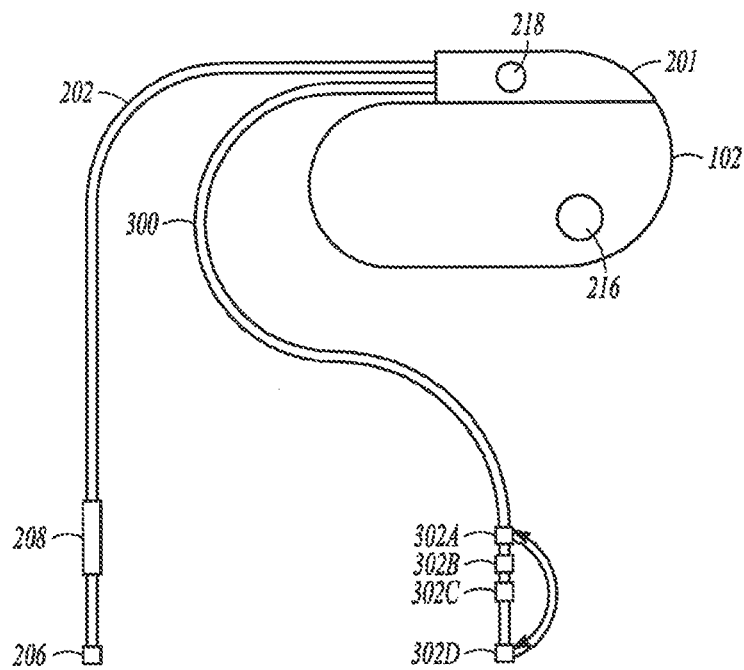
FIG. 3 shows an example of the implantable device connected at the header portion driving a RV intravascular leadwire and a LV/CS intravascular leadwire, such as for use in a "wide bipolar" pacing configuration.

FIG. 3 shows an example of the implantable device 102 connected at the header portion 201 to a RV intravascular leadwire 202 and a LV/CS intravascular leadwire 300. In some cases, the RV leadwire 202 can include one or more of an RV tip electrode 206, an RV ring electrode, an RV coil electrode 210, and an RA/superior vena cava (SVC) coil electrode. In an illustrative example that can include more than two electrodes, a quadripolar LV/CS leadwire 300 can include electrodes 302A-D, such as (e.g., listed proximally-to-distally) LV ring electrodes 302A, 302B, and 302C and an LV tip electrode 302D. In some cases, the body of the quadripolar LV/CS leadwire 300 is thin enough to be inserted into the coronary sinus, such that one or more of the electrodes 302A-D can be positioned at desired locations in association with the left ventricle, such as within the great cardiac vein or near the LV lateral free wall, such as to provide cardiac resynchronization therapy (CRT). The body of leadwire 300 may also include a distal portion having a shape-memory property, such as a tendency to spiral slightly, such as to impart a lateral mechanical bias force against one or more of the electrodes 302A-D, such as to position such one or more electrodes against a wall of the vasculature in which the distal portion of the leadwire 300 resides, such as to promote better capture of cardiac tissue from an electrostimulation or better intrinsic heart signal sensing.

In some cases, the spacing between the electrodes 302A-D may be significant. For example, the spacing between the most proximal LV ring electrode 302C and the most distal LV tip electrode 302D can be about 30 millimeters or even 35 millimeters. FIG. 3 illustrates an example of a "wide bipolar" pacing configuration, such as in which pacing pulses can be delivered between the proximal LV ring electrode 302A and the distal LV tip electrode 302D. A potential consequence of such a wide bipolar pacing configuration can be within-chamber anodal capture, such as which can occur when the anode electrode (e.g., LV tip electrode 302D) has a small surface area, leading to a large current density near the anode. Such within-chamber anodal capture can be unintentional or intentional.

When unintended, concurrent within-chamber anodal capture (e.g., at LV tip electrode 302D) and cathodal capture (e.g., at LV ring electrode 302A) can cause two intrinsic heart signal activation wave fronts propagating through the left ventricle. For a patient in which single-site pacing in the left ventricle (e.g., at the LV ring electrode 302A) is desired to better coordinate the right and left ventricular heart contractions, such dual-site anodal and cathodal capture may limit or reduce the benefit of the left-heart resynchronization, or may even result in less efficient blood pumping than would otherwise be obtained without such left-heart resynchronization. This illustrative example can be extended to pacing at more than two sites using anodal capture at one or more sites and cathodal capture at one or more sites.

By contrast, when intended, concurrent within-chamber anodal capture (e.g., at LV tip electrode 302D) and cathodal capture (e.g., at LV ring electrode 302A) can cause two intrinsic heart signal activation wave fronts propagating through the left ventricle, which may benefit certain patients by providing improved spatial coordination of the left ventricle, or improved spatial coordination of the left ventricle with the right ventricle, which may result in improved blood pumping. Moreover, for such a patient that can so benefit, the dual-site within-chamber anodal and cathodal capture may be accomplished using less energy (e.g., that of a single pace pulse) than might otherwise be used (e.g., if two separate cathodal-capture pace pulses were delivered at the two different sites). This illustrative example can be extended to pacing at more than two sites using anodal capture at one or more sites and cathodal capture at one or more sites.

When unintended, anodal capture can also affect other functionality of the implantable device 102. In an example, the implantable device 102 can be configured to include an automatic vector selection (AVS) capability, such as described in U.S. patent application Ser. No. 12/724,729, entitled ANODAL STIMULATION DETECTION AND AVOIDANCE, which is assigned to Cardiac Pacemakers, Inc., and which is incorporated by reference herein in its entirety for all purposes. In one example, the AVS can automatically choose the "best" or optimal electrode configuration (sometimes referred to as a "vector"), such as for delivering an electrostimulation, for sensing an intrinsic electrical heart signal, or for both delivering an electrostimulation and sensing an intrinsic heart signal. One or more criteria can be applied to select the "best" or optimal electrode configuration for electrostimulation. In some cases, threshold voltage for obtaining capture using a particular electrode configuration can be used as such a criterion for AVS, either alone, or with one or more other criteria, such as for comparing different electrode configurations in the AVS. For example, a particular electrode or electrode configuration maybe selected based, at least in part, on an electrode having the lowest capture threshold. In another example, information about whether a particular electrode configuration can capture a desired resulting heart contraction, without resulting in phrenic nerve stimulation—which can trigger a hiccup-like contraction of the diaphragm, which is usually undesired—can be used as a criterion for AVS, either alone, or with one or more other criteria, such as for comparing the different electrode configurations in the AVS.

Information about whether a particular electrode configuration results in one or more of anodal capture, cathodal capture, or both anodal capture and cathodal capture can be a useful input to AVS, for any of several reasons. In one example, such information can be used to intentionally select a configuration of two or more electrodes such as for intentionally providing a combination of both anodal and cathodal capture from at least two different local sites, such as described above or for intentionally avoiding such concurrent anodal and cathodal capture, such as described above. In another example, information about whether a particular electrode configuration results in one or more of anodal capture, cathodal capture, or both anodal capture and cathodal capture can be a useful input to AVS, such as to select an electrode configuration that avoids phrenic nerve stimulation, or that promotes the desired form of capture while avoiding phrenic nerve stimulation. For example, in the context of AVS, it may be desirable to ensure that the anode is not the electrode that is causing the phrenic nerve stimulation. In yet another example, information about whether a particular electrode configuration results in one or more of anodal capture, cathodal capture, or both anodal capture and cathodal capture can be a useful input to AVS, such as for selecting an electrode pair that has a lowest capture threshold (anodal or cathodal) for delivering an electrostimulation therapy.

FIGS. 4A-9 relate to various examples of detecting and/or discriminating between cathodal-only capture, anodal-only capture, and combined cathodal and anodal capture. Loss of anodal and/or cathodal capture also may be identified. In some examples, as will be described in detail below, after cathodal-only capture, anodal-only capture or a loss of both anodal and cathodal capture has been determined, the anodal and cathodal capture threshold values may be evaluated and compared to identify an electrode or electrode pair having the lowest capture threshold. Identifying the electrode or electrode pair having the lowest capture threshold may facilitate identification of an optimal pacing configuration that captures the heart while minimizing innervations of any of the surrounding tissue and that may utilizes the least amount of energy in an attempt to maximize battery life of the implantable medical device.

Figure 4A:
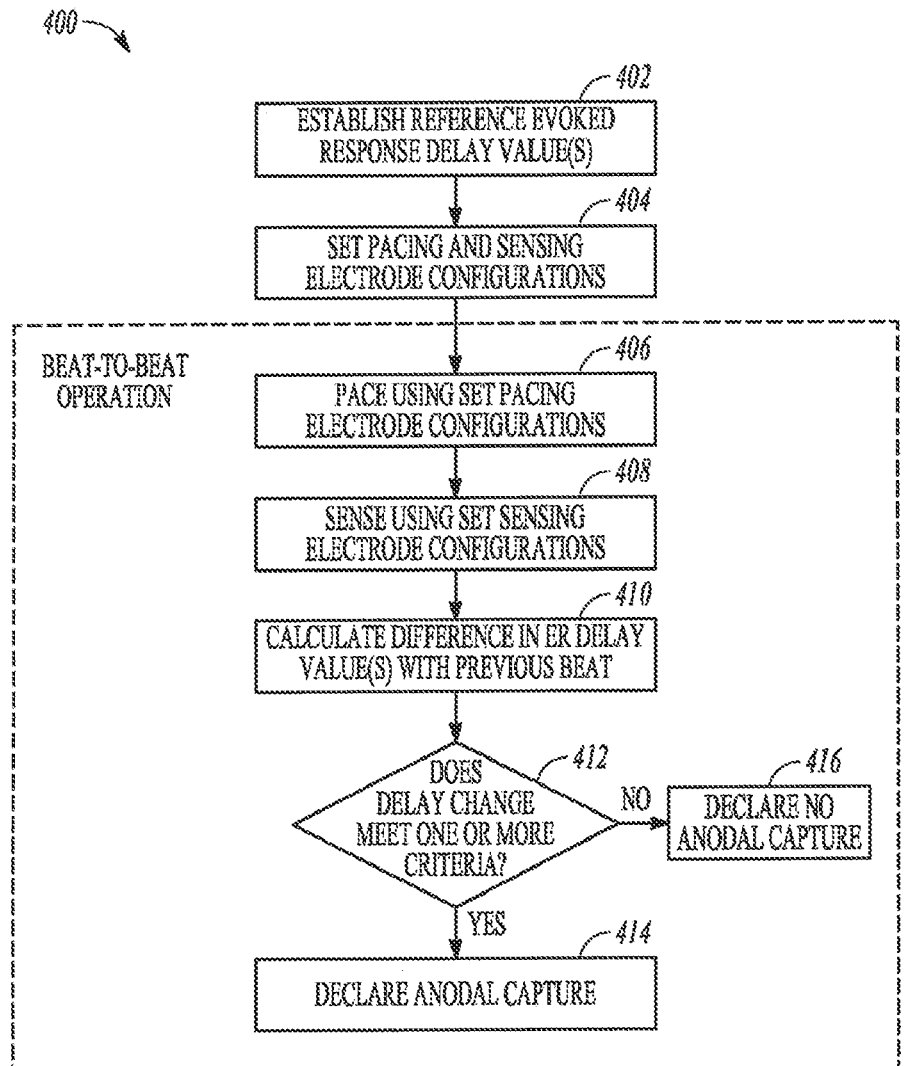
FIG. 4A shows an example of detecting at least partial anodal capture.

FIG. 4A shows an example 400 of detecting at least partial anodal capture. A cardiac signal sensing circuit (e.g., an atrial sensing circuit 108 or a ventricular sensing circuit 110) can detect an evoked response signal in response to electrostimulation. At 402, a first evoked response delay value can be established. In an example, this can include detecting (e.g., for a presumed anodal stimulation status) a time between an issued pace pulse and the resulting evoked response signal, or a feature thereof (e.g., first negative peak, most-negative peak, slope of the S-wave, or S wave width). The detected time interval for a single beat can be used, or a central tendency of such detected time intervals for multiple beats can be used. A presumed anodal stimulation status can be used, such as by using vastly different surface areas of the electrodes to help ensure that capture occurs at the smaller surface-area electrode. For example, this can include using a unipolar pacing configuration between a small surface area lead electrode and a large surface area "can" electrode. If the small surface area lead electrode is used as the negative electrode, then cathodal stimulation can be presumed. If the small surface area lead electrode is used as the positive electrode, then anodal stimulation can be presumed. In an example, establishing the first evoked response delay can include receiving the reference evoked response delay value from a user input, or from a manufacturer-specified or other pre-specified value.

At 404, a pacing electrode configuration, for which anodal capture information is desired, can be specified. A corresponding evoked response sensing electrode configuration, for obtaining information for determining the anodal capture information, can be specified. This can include choosing a sensing electrode that is located near the pacing electrode for which anodal capture is to be determined. In some cases, shared cathode sensing may facilitate discrimination between cathodal and anodal capture. Additionally, two sensing vectors (e.g. cathode and anode sensing) may facilitate an improved discrimination between cathodal capture and anodal capture.

At 406, paces can be issued, such as on a beat-to-beat basis using the specified pacing electrode configuration. At 408, a corresponding ER can be sensed, such as on a beat-to-beat basis using the specified sensing electrode configuration. The corresponding ER can be used to determine an ER delay, such as between the issued pace pulse and a like ER feature to that which was used to determine the reference ER delay at 402. The ER delay can be determined from a single beat, or a composite ER delay can be computed such as by using a central tendency of ER delay values, such as computed for several respective beats.

At 410, the ER delay or composite ER delay determined at 408 can be compared to the reference ER delay determined at 402, or to a delay previously computed at 408 for a beat or group of beats. At 412, a resulting difference can be compared to one or more criteria. If the difference exceeds one or more criteria, then, at 414, anodal capture can be declared, otherwise, at 416, it can be declared that no anodal capture is present.

Figure 4B:
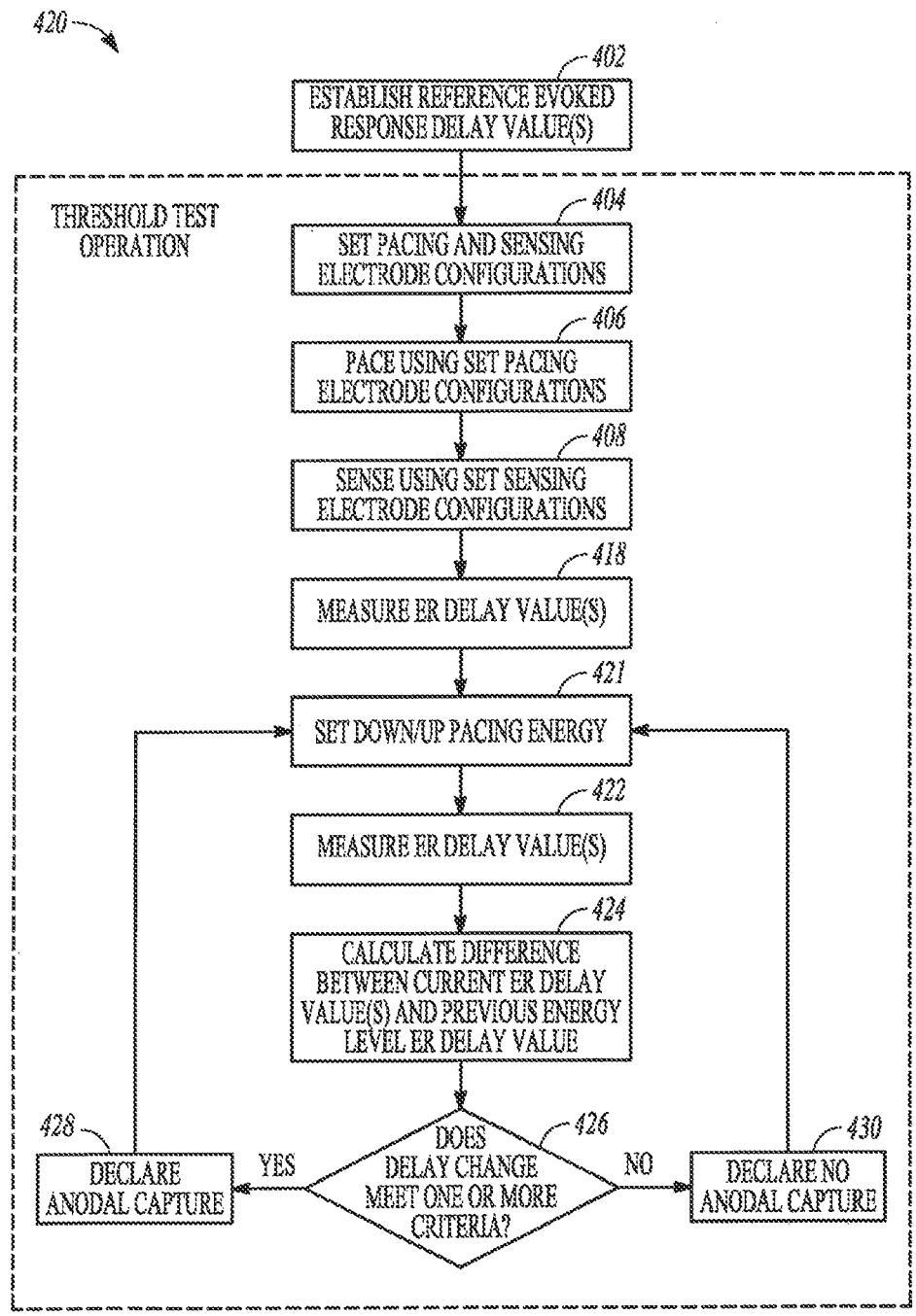
FIG. 4B shows an example of detecting at least partial anodal capture.

FIG. 4B shows an example 420 of detecting at least partial anodal capture, similar to that described above with respect to FIG. 4A, but focused on the context of a pacing energy threshold test, instead of being focused on the beat-to-beat operation described with respect to FIG. 4A. In FIG. 4B, at 402, a reference ER delay value can be established, such as described above with respect to FIG. 4A. At 404 of FIG. 4B, pacing and sensing electrode configurations can be established, such as described above with respect to FIG. 4A. At 406 of FIG. 4B, one or more pace pulses can be issued, such as described above with respect to FIG. 4A. At 408, corresponding ER signals can be sensed using the specified sensing electrode configuration, such as described above with respect to FIG. 4A. At 418, an ER delay value can be measured, such as described above with respect to 410 of FIG. 4A. At 421, a pacing energy (e.g., amplitude, pulse width, etc.) can be adjusted, such as by incrementally stepping it down (or up) such to an adjacent value in a set of available pacing energy values. At 422, the new pacing energy can be used to issue another pace, sense a resulting ER, and measure a resulting ER delay value, such as between the issued pace and a like ER feature to that which was used above in 418 and 402. At 424, the ER delay value can be compared to a corresponding value at the previous value of pacing energy. At 426, if the magnitude of the difference between the present and previous ER delay values meets one or more criteria, such as by exceeding a threshold amount, then, at 428, anodal capture can be declared, and process flow can return to 421, to repeat until one or more specified detection criteria (e.g., specified "X of Y" beats declared anodal captures) are met. At 426, if the magnitude of the difference between the present and previous ER delay values does not meet the one or more criteria, then, at 430, it is declared that the beat does not represent anodal capture, and process flow can return to 421, to repeat until one or more specified detection criteria (e.g., specified "X of Y" beats declared anodal captures) are met.

Figure 4C:
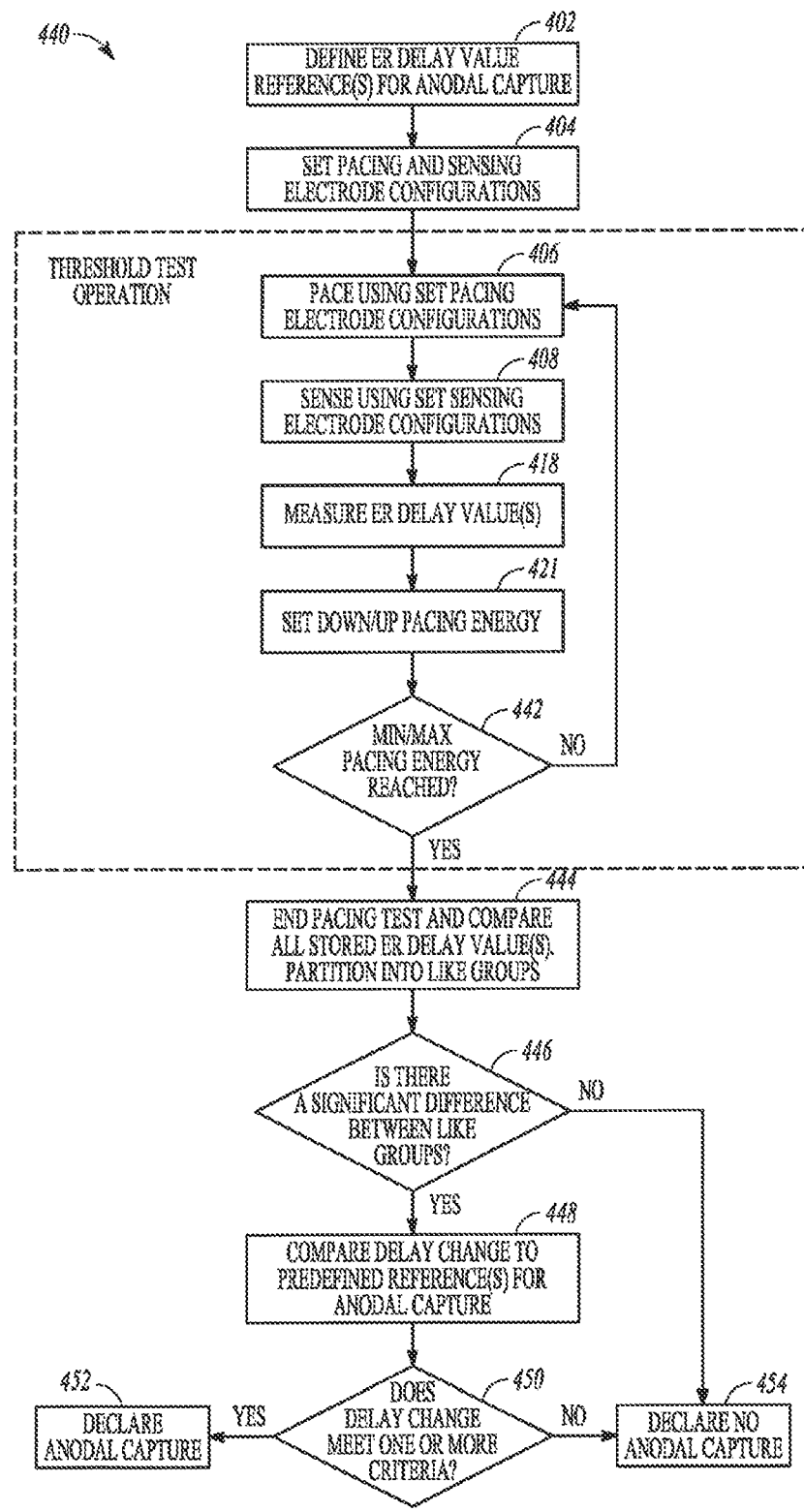
FIG. 4C shows an example of detecting at least partial anodal capture

FIG. 4C shows an example 440 of detecting at least partial anodal capture, similar to that described above with respect to FIG. 4A, but focused on the context of a pacing energy threshold test, instead of being focused on the beat-to-beat operation of FIG. 4A. At 402, an ER delay reference value can be determined, such as described above with respect to FIG. 4A. At 404, pacing and sensing electrode configurations can be specified, such as described above with respect to FIG. 4A. A pacing energy threshold test can commence, such as by issuing a pace at 406, such as described above with respect to FIG. 4A. At 408, a resulting ER can be sensed, such as described above with respect to FIG. 4A. At 418, an ER delay value can be measured, such as described above with respect to FIG. 4A, and stored. At 421, the pacing energy can be adjusted, such as stepped down (or stepped up), such as described above with respect to FIG. 4B. If the threshold test pacing energy limit (e.g., lower limit, where the pacing energy is being stepped down, or the upper limit, where the pacing energy is being stepped up) is not reached, process flow can return to 406, otherwise, process flow can proceed to 444. At 444, the pacing energy threshold test is ended. The stored ER delay values corresponding to the various pacing energies used during the pacing energy threshold test can be partitioned into like groups (e.g., groups exhibiting a similar ER delay value). At 446, it can be determined whether there is a significant difference between the like groups. If so, then at 448, the ER delay values can be compared to the ER delay reference value determined at 402. If the difference meets one or more criteria (e.g., if the reference value is representative of anodal capture, and the difference falls below a specified value with respect to the reference value), then anodal capture can be declared at 452. Otherwise, at 454, it can be declared that no anodal capture has occurred.

Figure 4D:
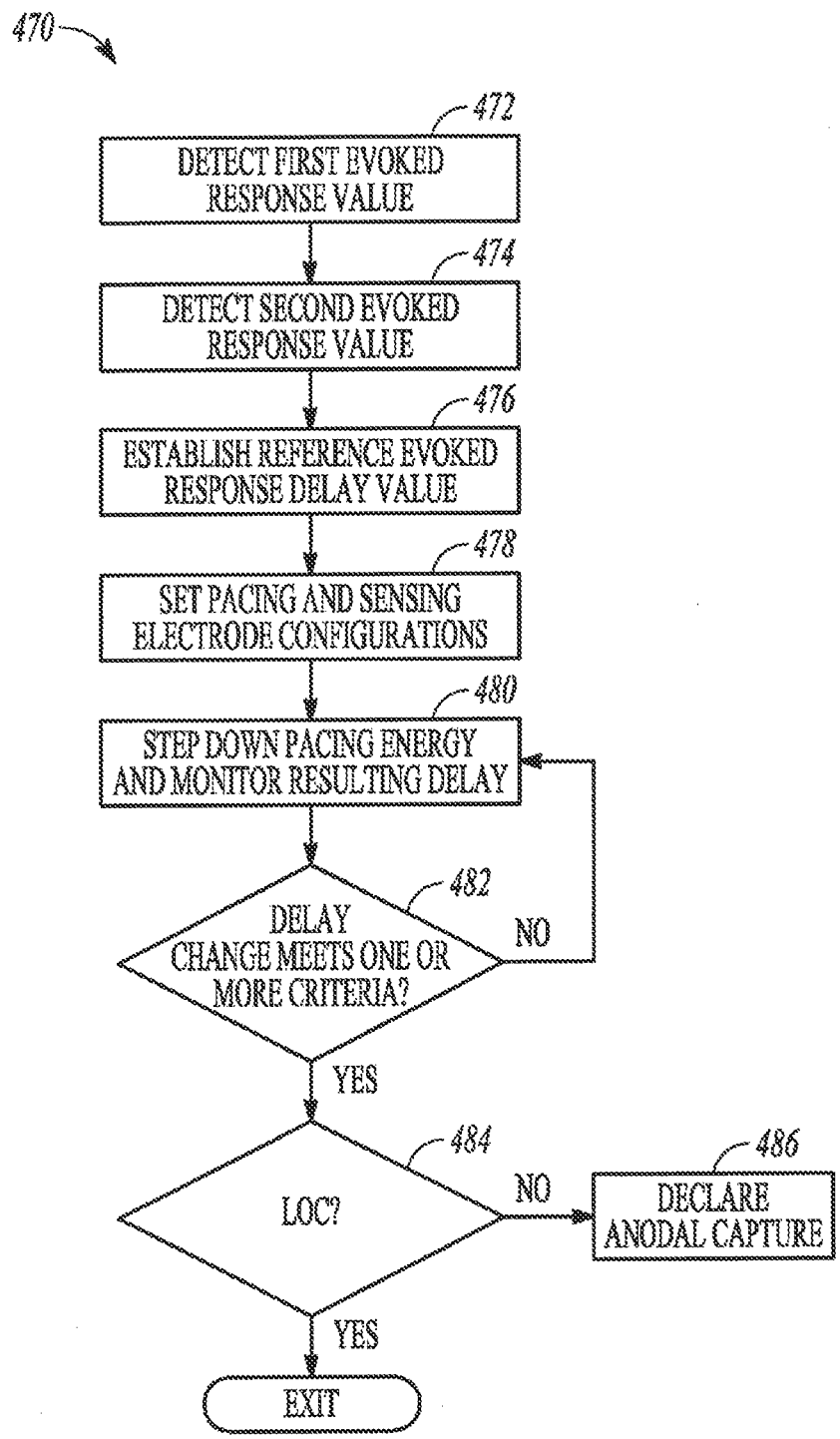
FIG. 4D shows an example of detecting at least partial anodal capture.

FIG. 4D shows an example 470 of detecting at least partial anodal capture. At 472, a first evoked response (ER) delay value can be detected. In an example, this can include detecting a time between an issued pace pulse and a resulting evoked response signal, or a specified feature thereof (e.g., first negative peak, most-negative peak, slope of the S-wave, or S wave width). In an example, this first ER delay can be measured in response to a pace delivered using a pacing electrode configuration that is unlikely to result in anodal capture, such as a unipolar pace between a cathodal LV electrode (e.g., one of LV ring electrode 214, LV tip electrode 212, LV ring electrode 302A-C, or LV tip electrode 302D) and a larger surface area "can" electrode 216 such as located at a housing of the electronics unit of the implantable device 102. Because the can electrode 216 has a substantially larger surface area than the cathodal LV electrode, and is generally pectorally-located at a substantial distance away from the heart, capture does not occur at the can electrode 216. Instead, capture only occurs at the cathodal LV electrode. By applying a negative voltage to the LV electrode, rendering it cathodal, any resulting capture will be cathodal. In this way, the first ER delay value can be representative of an ER delay that is associated with cathodal LV capture.

For sensing the ER delay, a sensing electrode configuration can be used that includes at least one electrode that is located close to a "candidate" electrode for which the presence or absence of stimulation is to be determined, or distant from another electrode with which the candidate electrode is to be used. In an example in which it is desired to be determine whether anodal capture is occurring at the RV ring electrode 208 when the RV ring electrode 208 is used as the anode together with an LV electrode (e.g., 212, 214, or one or more of 302A-D) as the cathode to deliver a pace, the ER sensing can be between the RV tip electrode 206 and a can electrode 216 or a header electrode 218. In this example, the RV tip electrode 206 is close to the candidate RV ring electrode 208 (to be tested for anodal capture) and distant from the LV electrode (e.g., 212, 214, or one or more of 302A-D) that is to be used together with the candidate RV electrode 208 to deliver the pace. In some cases, a second sensing vector may also be selected. As discussed above, two sense vectors may facilitate improved discrimination between cathodal capture and anodal capture.

In an example in which the ER delay is measured between an issued pace and a resulting specified feature of the ER, some illustrative examples of such a feature can include a start of activation (e.g., such as can be determined by a level-detector circuit), a positive or negative peak of activation (e.g., such as can be determined by a peak detector circuit), or some other feature.

At 474, a second ER delay value can be detected. In an example, this can include detecting a time between an issued pace pulse and a resulting evoked response signal, or a specified feature thereof—such as a like feature to that described above with respect to 472. This second ER delay can be measured using the candidate electrode to deliver a unipolar pace together with a can electrode 216. Again, because of the different electrode surface areas and the substantial distance between the can electrode 216 and the heart, capture will occur at the candidate electrode. Such capture will be cathodal when the candidate electrode is negative with respect to the can electrode 216 during the pace, and will be anodal when the candidate electrode is positive with respect to the can electrode during the pace. Either can be used, but cathodal stimulation at the can electrode 216 may be uncomfortable, and it should be noted that it is believed that anodal stimulation may propagate through tissue faster than cathodal stimulation. In any case, the resulting second ER delay will be representative of capture occurring at the candidate electrode. By contrast, the first ER delay described with respect to 472 will be representative of LV capture occurring away from the candidate electrode and the second ER delay will be representative of capture occurring at the candidate electrode. Since the unipolar sensing electrode (e.g., RV tip electrode 206) is closer to the candidate electrode than it is to the LV electrode to be used together with the candidate electrode, the second ER delay will be shorter than the first ER delay. Conversely, a different electrode configuration can be used in which the unipolar sensing electrode is farther from the candidate electrode and closer to the other electrode, in which case the first ER delay will be shorter than the second ER delay.

At 476, a reference ER delay value can be established, such as for later use to determine whether capture is occurring at or away from the candidate electrode. The reference ER delay can be established to be a specified (e.g., fixed percentage, etc.) increment shorter than the first ER delay value. In some he measured reference ER delay need not be generated using a single measurement, but can instead be generated using multiple measurements, such as a mean, median, or other central tendency of multiple measurements. In other cases, the reference ER delay can be established to be a specified (e.g., fixed, percentage, etc.) increment longer than the second ER delay value. In still other cases, the reference ER delay can be established to be a desired fraction (e.g., midway) of the temporal distance between the first and second ER delay values.

At 478, the pacing and sensing electrode configurations can be established, such as for use in providing a step-down (or step-up) pacing energy threshold test, or on a beat-to-beat basis without requiring a pacing energy threshold test. In an example in which the candidate electrode being tested for anodal capture is the RV ring electrode 208, used in an extended bipolar pacing configuration with the other electrode being the LV ring electrode 214 (by way of example), a unipolar sensing configuration between the RV tip electrode 206 and the can electrode 216 can be used, such as described above.

At 480, the pacing energy can be set to an initial value, such as at or near the top of the pacing energy range. Then, the pacing energy can be stepped down and the resulting ER delay can be monitored. Conversely, the pacing energy can be set to an initial value, such as at or near the bottom of the pacing range, then the pacing energy can be stepped up and the resulting ER delay can be monitored. This can be done as part of a pacing energy threshold test, or on a beat-to-beat basis without requiring a pacing energy threshold test.

At 482, the resulting ER delay can be compared to one or more criteria, such as to the reference ER delay that was established at 406. If the resulting ER delay meets the criteria, such as by exhibiting a shift from longer than the reference ER delay to shorter than the reference ER delay, or vice-versa, then a change in capture is suspected. Otherwise, if the resulting ER delay does not meet the criteria, then the pacing energy can again be stepped down at 410 and the resulting delay can be monitored.

At 484, it can be determined whether complete LOC has occurred, such as by using existing automatic capture verification technique, such as described in Meyer et al., U.S. Pat. No. 7,711,424, entitled SELECTION OF CARDIAC SIGNAL FEATURES DETECTED IN MULTIPLE CLASSIFICATION INTERVALS FOR CARDIAC PACING RESPONSE CLASSIFICATION, which is incorporated herein by reference. If at 484 no complete LOC has occurred, then at 486 it can be declared that anodal capture is likely present at the RV ring electrode 208 at energies that are greater than or equal to the particular pacing energy being used. Otherwise, at 482, if complete LOC has occurred, then it can be declared that cathodal capture at the LV ring electrode 214 (unaccompanied by anodal capture at the RV ring electrode 208) is likely present at energies that are greater than the particular pacing energy being used when the onset of complete LOC occurred.

In this way, by using a sensing electrode that is closer to a first pacing electrode than to a second pacing electrode, a shift in a resulting ER time can be used to determine whether one (or both) of these first and second pacing electrodes (or which one) is actually capturing nearby cardiac tissue. Since the polarity of the signals applied at the first and second pacing electrodes can be specified, such information can be used with the capture information to determine whether anodal capture is occurring, cathodal capture is occurring, or both anodal and cathodal capture are occurring.

If the pacing energy is being stepped down, a likely scenario can be that the resulting ER delay shifts from shorter (because the RV ring electrode 208 is exhibiting anodal capture at such higher pacing energies) to longer (when the RV ring electrode ceases anodal capture, and cathodal-only capture occurs at the LV ring electrode 214). It is believed that the ER delay can become even longer when complete LOC occurs (e.g., the LV ring electrode 214 is no longer exhibiting cathodal capture).

As a variation to the example describe above, detecting the first and second ER values at 402 and 404 can be replaced or augmented by detecting corresponding first and second ER signal templates. Then, at 412, the monitored ER morphology can be compared to one or both of the templates, such as by performing a correlation function. If the monitored ER morphology exhibits a sufficient shift away from the first ER signal template, or a sufficient shift toward the second ER signal template, or both, then a corresponding change in capture can be declared. Such replacing or augmenting an ER value (which can be compared to a reference value) with an ER signal template (to which a correlation function or other similarity calculation can be performed) can be extended to the ER values of various other examples described in this document.

Figure 5:
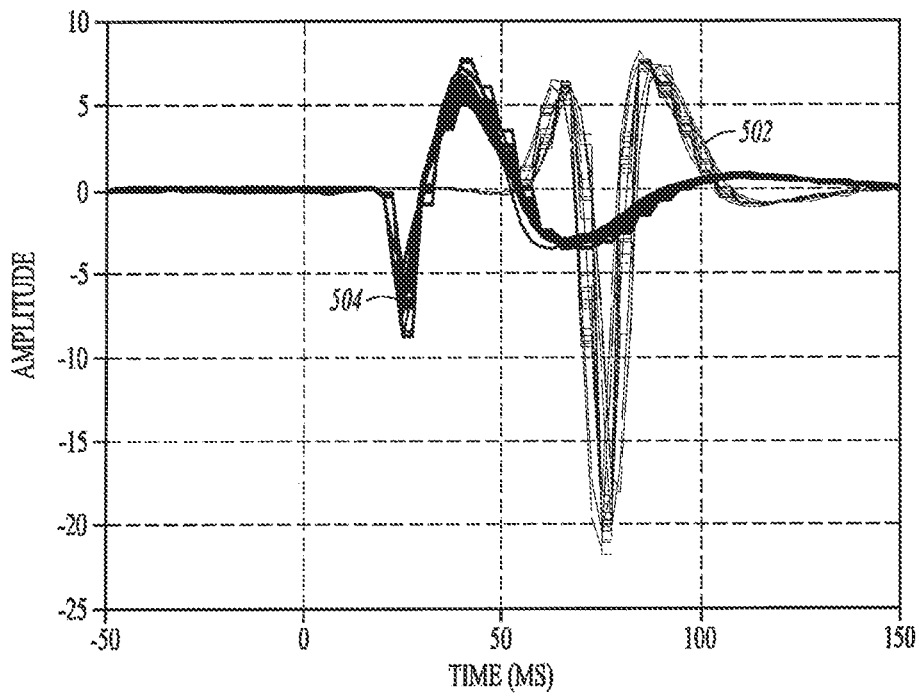
FIG. 5 is an amplitude vs. time graph showing multiple tracings of ER signals resulting from cathodal-only capture and multiple tracings of ER signals resulting from combined anodal and cathodal capture.

FIG. 5 is an amplitude vs. time graph showing multiple tracings 502 of ER signals resulting from cathodal-only capture and multiple tracings 504 of ER signals resulting from combined anodal and cathodal capture. In the graph of FIG. 5, the pace pulse is issued at time t=0. For this example, extended bipolar pacing was delivered between the RV ring electrode 208 and one of the LV ring electrode 214 and the LV tip electrode 212, with the LV electrode being more negative than the RV electrode during the pace pulse. The ER signal was sensed using a unipolar sensing configuration between the RV tip electrode 206 and the can electrode 216.

In the example of FIG. 5, the combined anodal and cathodal capture ER signals 504 collectively exhibit an approximately 25 millisecond shorter delay from the preceding pace pulse than the cathodal-only capture ER signals 502, along with a noticeably different signal morphology. Such data supports the above-described examples, indicating that either the shift in time delay or change in ER signal morphology (or both) can be used to discriminate between cathodal-only capture, anodal-only capture, and combined anodal and cathodal capture.

Figure 6:
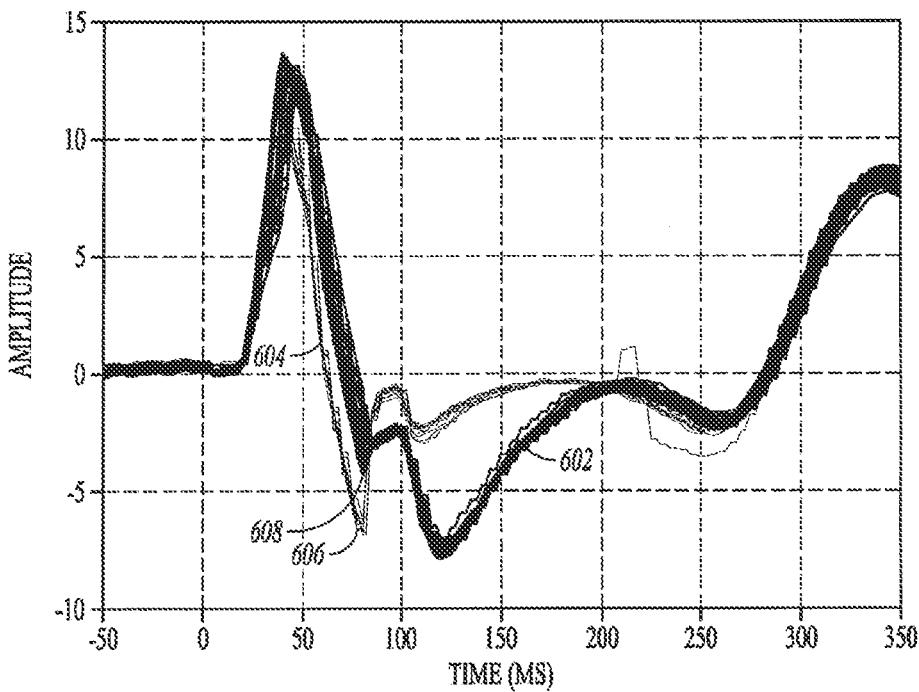
FIG. 6 is an amplitude vs. time graph showing multiple tracings of cathodal-only capture ER signals and combined anodal and cathodal ER signals.

FIG. 6 is an amplitude vs. time graph showing multiple tracings of (1) cathodal-only capture ER signals 602 and (2) combined anodal and cathodal ER signals 604. In an example, such as illustrated with respect to FIG. 6, the candidate electrode being tested to determine whether anodal capture is occurring can be the RV ring electrode 208, which can be used in an extended bipolar pacing configuration with one of the LV ring electrode 214 or the LV tip electrode 212, with unipolar ER signal sensing carried out between the can electrode 216 and the other one of the LV ring electrode 214 and the LV tip electrode 212.

In the example of FIG. 6, differences can be observed between the cathodal-only capture ER signals 602 and the combined anodal and cathodal ER signals 604. In particular the first negative peak 606 of the combined anodal and cathodal ER signals 604 occurs some time (e.g., 30 to 40 milliseconds, although this can vary) earlier than the corresponding first negative peak 608 of the cathodal-only capture ER signals 602. Such a time difference can be used to detect a shift from cathodal-only capture to combined anodal and cathodal capture, or vice-versa. Moreover, such a difference in the ER signal can be used in either a cross-chamber (e.g., extended bipolar) setting, such as shown in FIG. 2, or in a within-chamber (e.g., LV quadripolar such as shown in FIG. 3, RV bipolar, etc.) setting such as to perform such discrimination between cathodal-only capture, anodal-only capture, and combined anodal and cathodal capture.

Figure 7:
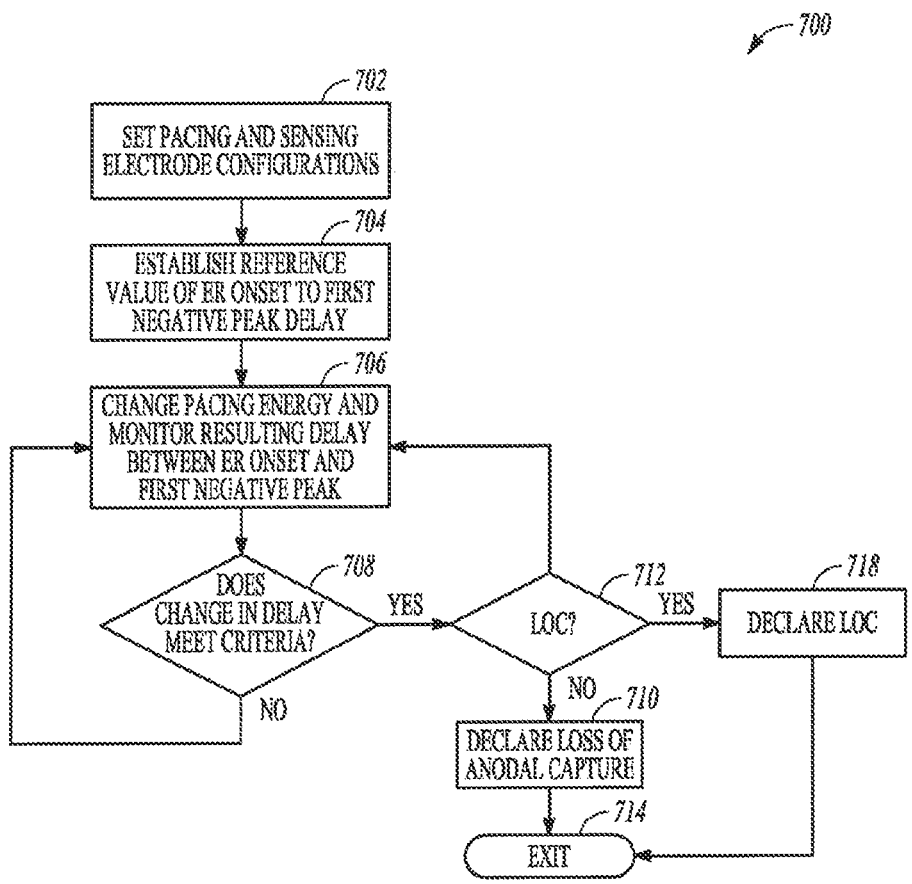
FIG. 7 shows an example of detecting anodal capture, such as by using the temporal shift of the first negative peak of the ER signal, such as shown in FIG. 6.

FIG. 7 shows an example 700 of detecting anodal capture, such as by using the temporal shift of the first negative peak of the ER signal, such as shown in FIG. 6. At 702, pacing and sensing electrode configurations can be set, such as appropriate for obtaining a reference value of the time interval between (1) a reference fiducial, such as the onset of the ER activation and (2) the first negative peak of the ER signal. In one example, the pacing and sensing electrode configurations can be set such that the reference value of the time interval can be obtained in a manner such that it is known whether anodal stimulation is occurring, such as described above. In an example, the candidate electrode being tested to determine whether anodal capture is occurring can be the RV ring electrode 208, which, in an example, can be used in an extended bipolar pacing configuration with at least one of the LV ring electrode 214 or the LV tip electrode 212 (or other left ventricular electrode, such as with a multipolar, e.g., quadripolar, LV lead), with unipolar ER signal sensing carried out between the can electrode 216 and the other one of the LV ring electrode 214 and the LV tip electrode 212. At 702, the pacing and sensing electrode configurations can be set accordingly.

At 704, the pacing and sensing electrode configurations of 702 can be used to obtain a reference value of the time interval between (1) the onset of the ER activation and (2) the first negative peak of the ER signal. This can include using the controller circuit 116 to direct the ventricular therapy circuit 114 to issue a pacing pulse, such as using the pacing electrode configuration described above, and using the controller circuit 116 to direct the ventricular sensing circuit 112 to sense the ER signal. The resulting ER signal can be analyzed, such as by using signal processing circuitry that can be provided by the controller circuit 116 or elsewhere, such as to detect the onset of the ER activation (e.g., using a level detector circuit that can be provided by such signal processing circuitry) and to detect the subsequent first negative peak of the ER signal (e.g., using a peak-detector circuit that can be provided by such signal processing circuitry), and measuring a time difference between the onset of the ER activation and the subsequent first negative peak of the ER signal. This measured time difference can be used as a reference time difference, such as to which later time difference measurements can be compared. As explained above, the reference time difference can be obtained under a known condition of whether anodal stimulation is present, which can provide useful contextual information as other measurements later deviate toward or away from the reference time difference value. In an example, the measured reference time difference need not be generated using a single measurement, but can instead be generated using multiple measurements, such as a mean, median, or other central tendency of multiple measurements. In an example, multiple measurements used to generate the reference time difference can be made using like pacing energies, such as at a large pacing energy value, for example, maximum pacing amplitude at a nominal pacing pulse width (e.g., 0.4 milliseconds or 0.5 milliseconds).

At 706, the pacing energy can be adjusted, for example, decreased, such as by stepping the pacing energy down incrementally. In an example, this can include decreasing the pacing amplitude incrementally while maintaining a specified pacing pulse width, or vice-versa. In one example, at each such step, an ER signal is obtained, and the time difference between the onset of the ER activation and the subsequent first negative peak can be obtained. As described above with respect to the reference time difference, for a particular pacing energy step this can be determined using a single measurement, or by computing a central tendency or otherwise combining the time differences resulting from multiple individual measurements, such as from corresponding multiple ER signals associated with corresponding multiple paces.

At 708, the resulting measured time difference (or resulting combined measured time difference) can be compared to one or more criteria. In one example, this can include comparing the resulting measured time difference to a threshold value that can be based upon the reference time difference, such as a percentage thereof, a fixed offset therefrom, or the like. In an illustrative example, it can be known or assumed that anodal capture is occurring when the maximum pacing energy is delivered, such as for obtaining the reference time difference value at 704. In such a case, if at 708 the measured time difference increases above a specified percentage (e.g., 120%) of the reference time difference, then loss of anodal capture can be declared, and at 712, it can be determined whether complete loss of capture (LOC) has occurred at that particular increment of pacing energy. If there is no complete LOC, then at 710, loss of anodal capture can be declared, and the example 700 can be exited at 714 (or can return to 706 if it is desired to also locate the energy at which complete LOC occurs). At 712, if there is complete LOC, then complete LOC can be declared at 718, and the example 700 can exit at 714. At 708, if the measured time difference does not meet the criteria (e.g., does not increase above 120% of the reference time difference value), then there can be a return to 706, and the pacing energy can be stepped down again, while monitoring the resulting ER signal to measure the resulting delay between the ER activation onset and the subsequent first negative peak, as described above.

Figure 8:
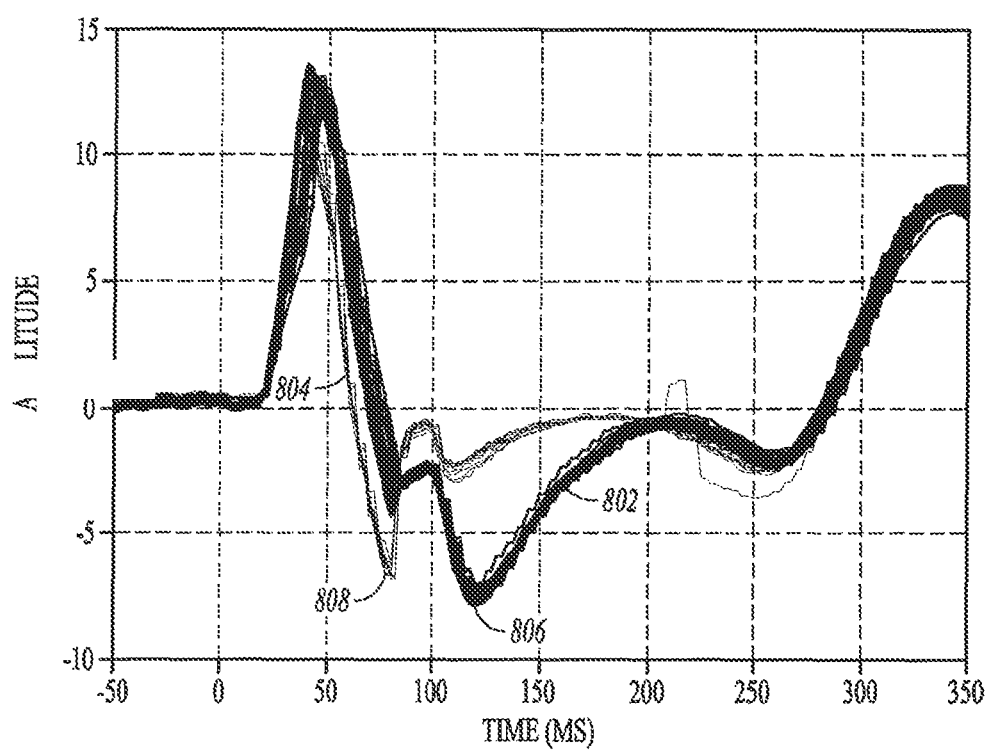
FIG. 8 is an amplitude vs. time graph showing multiple tracings of cathodal-only capture ER signals and combined anodal and cathodal ER signals.

In the example of FIG. 7, the same pacing electrode configuration and sensing electrode configuration can be used both for determining the reference time difference at 704 and for determining the later time differences at 706. However, this is not required. In one example, a different electrode configuration can be used for obtaining a reference time difference than for determining a later time difference. For example, FIG. 8 is an amplitude vs. time graph showing multiple tracings of (1) cathodal-only capture ER signals 802 and (2) combined anodal and cathodal ER signals 804. In this example, the various ER signal tracings are temporally aligned, such as according to a previous pace or according to the onset of the ER activation. In an example, such as illustrated with respect to FIG. 8, the cathodal-only ER signals 802 can be used to form an ER signal reference template, such as can be obtained by delivering a unipolar LV pace, such as between a cathodal LV ring electrode 214 and an anodal can electrode 216, and unipolar ER signal sensing carried out between the can electrode 216 and the LV tip electrode 212. Delivering the unipolar LV pace in this manner assures that no anodal capture occurs, because of the distance between the anodal can electrode 216 and the excitable heart tissue, and the relatively larger surface area of the can electrode relative to the cathodal LV ring electrode 214. In this example, a reference time difference can be measured between the ER activation onset and the absolute minimum (e.g., the most negative peak 806) of the ER waveform (which is not necessarily the same as the first negative peak of the ER waveform described above with respect to FIG. 6).

Then, during a pacing energy threshold or capture test, or on a beat-to-beat basis outside of a threshold or capture test, a candidate electrode configuration can be tested to determine whether anodal capture is occurring. In an example, the candidate electrode being tested to determine whether anodal capture is occurring can be the RV ring electrode 208, which can be used in an extended bipolar pacing configuration with the same pacing cathode as was used to obtain the reference signal (e.g., such as the same LV ring electrode 214 used as the cathode in obtaining the reference signal, above), with unipolar ER signal sensing carried out between the can electrode 216 and an electrode near the pacing cathode (e.g., sensing using the LV tip electrode 212 when the LV ring electrode 214 is used as the pacing cathode). For each incremental change in the pacing energy, a time difference can be measured between the onset of the ER activation and the absolute minimum (e.g., the most negative peak 808) of the ER waveform (which is not necessarily the same as the first negative peak of the ER waveform described above with respect to FIG. 6). When the capture is at least in part anodal, the time difference will be considerably shorter than the reference time difference, such as, for example, about 40 milliseconds shorter as shown in the example of FIG. 8, although this number can vary, such as between patients. Thus, by comparing the time difference obtained using the ER signal 804 after the incremental change to one or more criteria derived from the reference time difference obtained using the ER signal 802, when the time difference drops below the reference time difference by more than a relative threshold value (e.g., 80% of the reference time difference) or by more than a fixed threshold value (e.g., by at least 25 milliseconds), then at least partial anodal capture can be declared. This can be based upon a single measurement, or multiple measurements (e.g., a central tendency), for either the reference time difference, or for the actual time differences obtained during various pacing energies.

Figure 9:
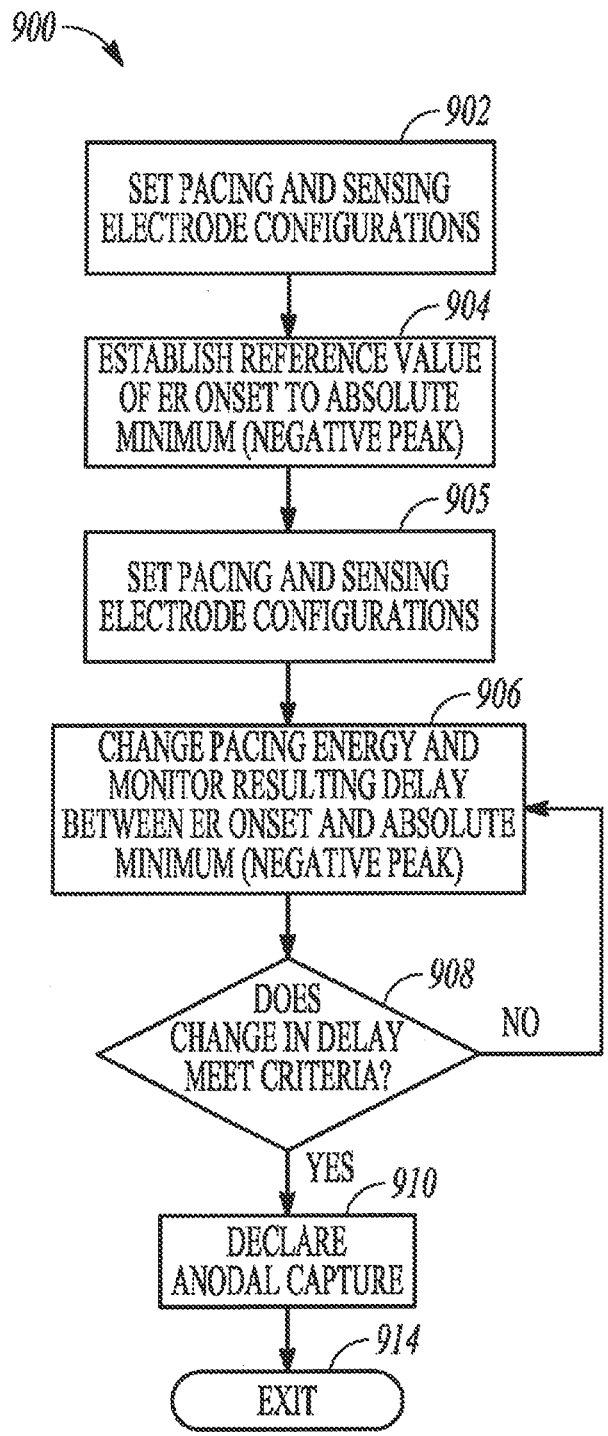
FIG. 9 is a flow chart of a method of detecting anodal capture using the temporal shift of the absolute minimum negative peak of an ER signal, such as shown in FIG. 8.

FIG. 9 shows an example 900 of detecting at least partial anodal capture, such as by using the temporal shift of the absolute minimum negative peak of the ER signal, such as shown in FIG. 8. At 902, pacing and sensing electrode configurations can be set, such as appropriate for obtaining a reference value of the time interval between (1) the onset of the ER activation and (2) the absolute minimum (most negative peak) of the ER signal, such as in a unipolar pacing and sensing configuration such as described above, for example, with respect to FIG. 8.

At 904, the pacing and sensing electrode configurations of 902 can be used to obtain a reference value of the time interval between (1) a reference fiducial, such as the onset of the ER activation and (2) the absolute minimum (most negative peak) of the ER signal, similar to that described above at 704, but using the absolute minimum (most negative peak) of the ER signal. This measured time difference can be used as a reference time difference, such as to which later time difference measurements can be compared, similar to that described above at 704, but using the absolute minimum (most negative peak) of the ER signal.

At 905, the pacing configuration can be changed, such as to apply the pacing configuration of interest for determining whether at least partial anodal capture is occurring. In an example, this can include placing the pacing electrode configuration into an extended bipolar pacing configuration, such as using the RV ring electrode 208 with the same one of the LV ring electrode 214 or the LV tip electrode 212 that was used as a pacing cathode for determining the reference value of the time interval at 904 with unipolar ER signal sensing carried out between the can electrode 216 and the other one of the LV ring electrode 214 and the LV tip electrode 212.

At 906, the pacing energy can be changed, similar to that described above with respect to 706, and a responsive ER signal fiducial can be acquired, such as described above, but using the absolute minimum (most negative peak) of the ER signal.

At 908, the resulting measured time difference (or resulting combined measured time difference) can be compared to one or more criteria, such as described above with respect to 708, although different criteria can be experimentally or otherwise determined and used here.

In an illustrative example, if at 908 the measured time difference falls below 80% of the reference time difference, then at 910, at least partial anodal capture can be declared, and at 914, the example 900 can be exited. Otherwise, there is a return to 906, and the pacing energy can be changed (e.g., stepped down) again, while monitoring the resulting ER signal to measure the resulting delay between the ER activation onset and the absolute minimum (most negative peak), as described above with respect to FIGS. 8 and 9.

Various techniques for detecting and/or discriminating between cathodal-only capture, at least partial anodal capture, and combined cathodal and anodal capture are described with reference to FIGS. 4A-9. These are just some examples. Other methods and techniques for detecting and/or discriminating between cathodal-only capture, at least partial anodal capture, and combined cathodal and anodal capture are shown and described in co-pending U.S. Published Application No. 2012/0130442, filed on Nov. 21, 2011, entitled "CARDIAC ANODAL STIMULATION DETECTION", which is hereby incorporated by reference in its entirety for all purposes.

Any one of the methods used to and/or discriminating between cathodal-only capture, at least partial anodal capture, and combined cathodal and anodal capture, as described herein with reference to FIGS. 4A-9, may be utilized in connection with a method of determining an optimal electrode configuration for delivering an electrostimulation therapy. In some examples, after cathodal-only capture, anodal-only capture or a loss of both anodal and cathodal capture has been determined, the anodal and cathodal capture threshold values may be evaluated and compared to identify an electrode or electrode pair having the lowest capture threshold. Identifying the electrode or electrode pair having the lowest capture threshold may facilitate identification of an optimal pacing configuration that captures the heart while minimizing innervations of any of the surrounding tissue and that may also utilize the least amount of energy in an attempt to maximize battery life of the implantable medical device.

Figure 10A:
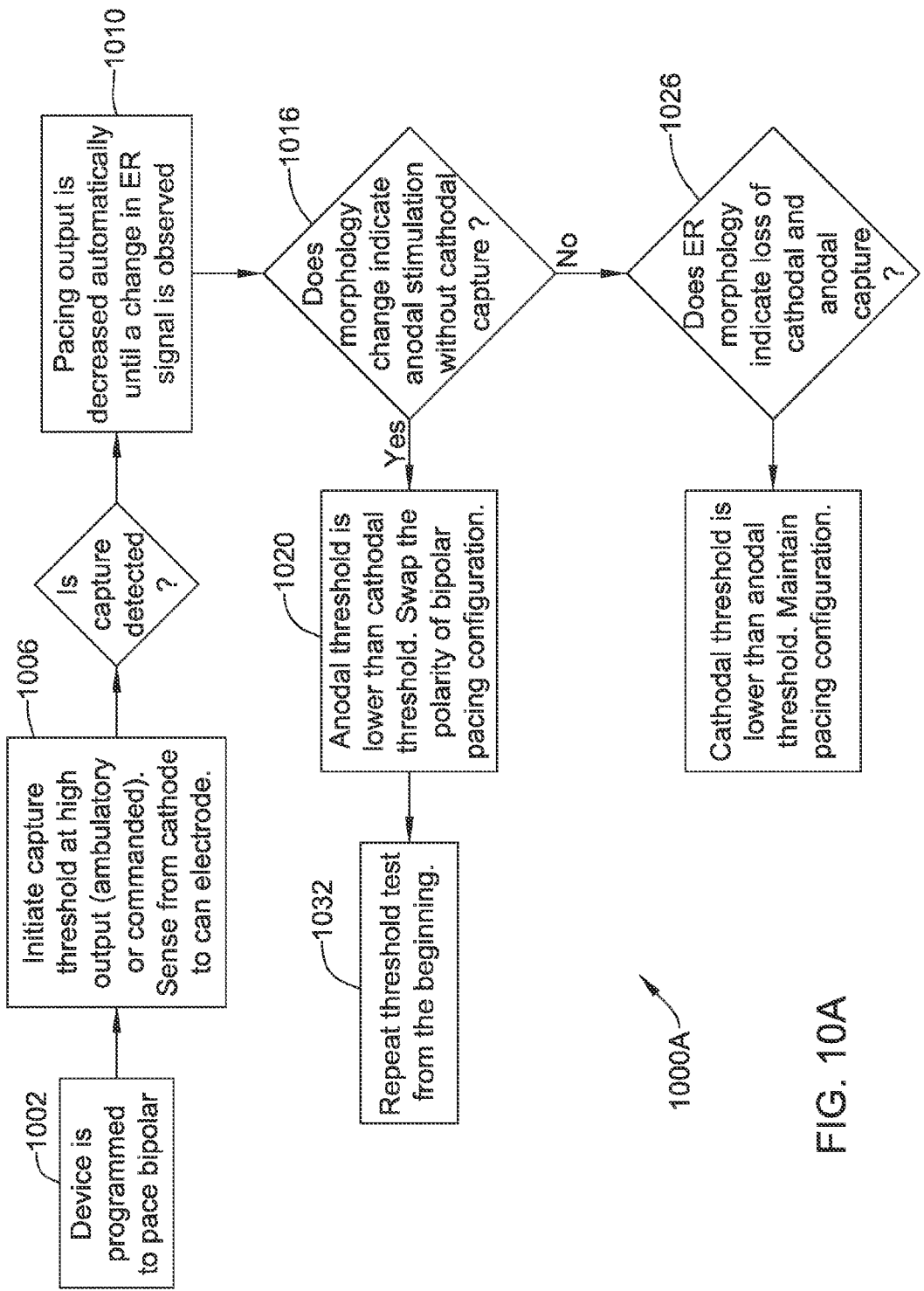
FIGS. 10A and 10B are flow charts of example methods for identifying an electrode from at least two or more electrodes that has a lower capture threshold for delivering an electrostimulation therapy.
Figure 10B:
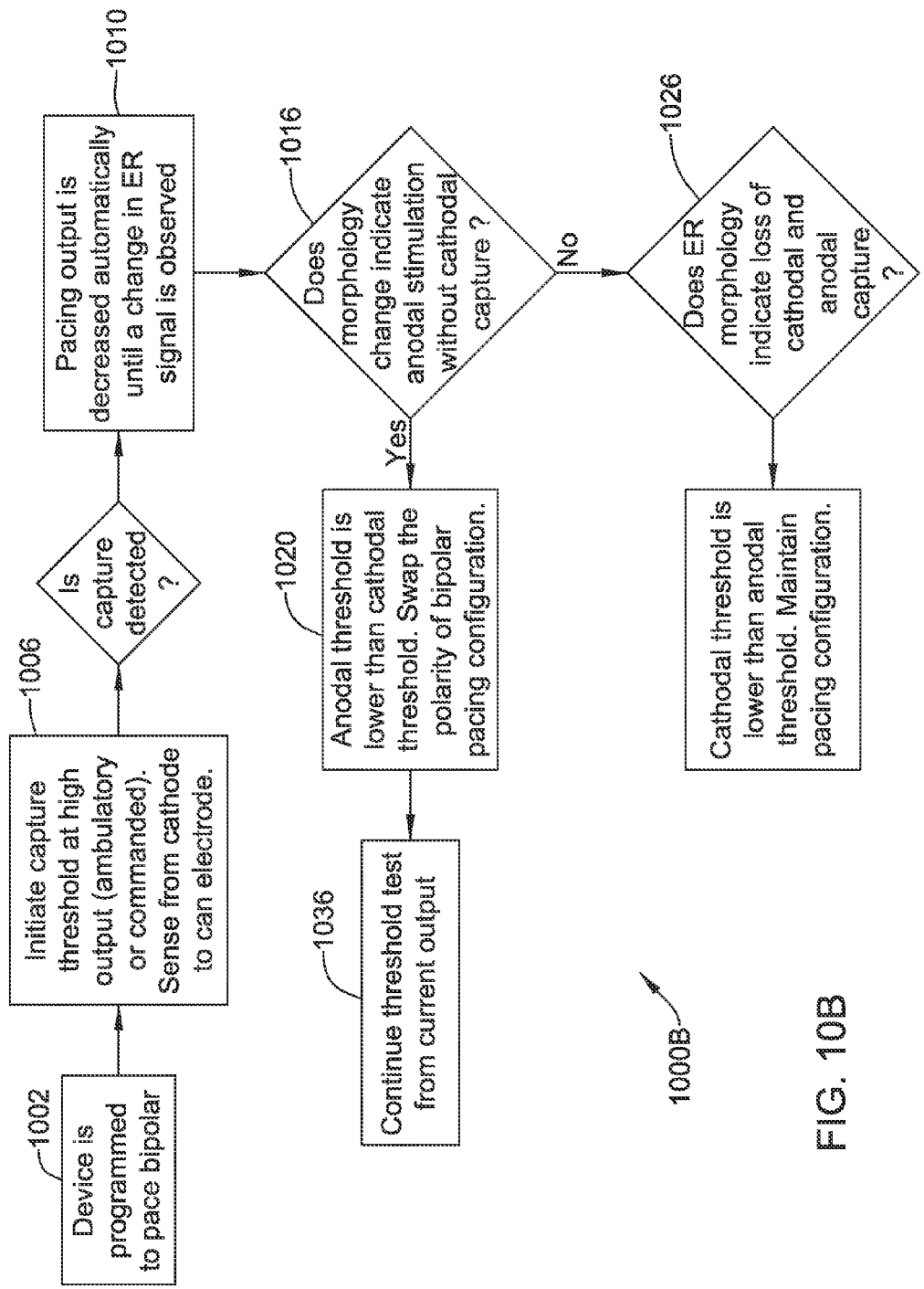

FIGS. 10A and 10B show two example methods 1000A and 1000B for identifying an electrode from at least two or more electrodes that has the lowest capture threshold for delivering an electrostimulation therapy. The electrode that is ultimately identified through execution of the methods may initially be either an anode or a cathode electrode at the beginning of the testing process.

In the example shown in FIG. 10A, at 1002 an implantable medical device such as, for example, IMD 102, can be programmed for bipolar pacing. At 1006, capture threshold testing is initiated at a sufficient energy output level so as to cause a combined cathodal and anodal capture of the heart, which may result in a shared cathode and anode evoked response (ER) signal such as can be seen, for example, in FIGS. 6 and 8. In some cases, the capture threshold test that is initiated by the IMD 102 may be a step-down capture threshold test, where the pacing pulse energy is stepped down.

At 1010, during the step-down capture threshold test, the pacing output energy of the pacing pulses is decreased automatically until a change in the ER signal is detected by the processor 116. The change in ER signal may be a temporal change or time shift in a selected peak, as described herein with reference to, for example, FIGS. 6 and 8. At 1016, upon detecting a change in the ER signal, the processor 116 may be further configured to determine if the detected change in the ER signal indicates anodal only capture without cathodal capture (i.e. loss of cathodal capture) or loss of both anodal and cathodal capture, as described herein with reference to, for example, FIGS. 7 and 9.

If a change in the ER signal indicates anodal-only capture, then the anodal capture threshold is considered to be lower than the cathodal capture threshold. In response to detecting anodal-only capture, at 1020, the processor 116 may be programmed to re-assign or switch the polarity of the initial anode and cathode selected for testing. For example, the processor 116 may use the electrode initially identified as the anode as the cathode for any subsequent capture threshold testing. Similarly, the processor 116 may use the electrode initially identified as the cathode as the anode for any subsequent capture threshold testing.

In some cases, the capture threshold test may be repeated after re-assignment of the polarity of the electrodes. In some cases, as indicated at 1032 in FIG. 10A, the capture threshold test may be repeated after the switch in polarity of the initial anode and cathode beginning with from a higher pacing output level, such as indicated at 1006, so as to ensure both anodal and cathodal capture. In other cases, as indicated at 1036 in FIG. 10B, the processor 116 may be programmed to continue capture threshold testing from a current energy output level after the switch in polarity. Because the second method of FIG. 10B begins capture threshold testing at an energy level that is lower than the initial energy level after the switch in polarity, it may require less time to identify the lowest capture threshold.

If the processor 116 determines that the change in ER signal indicates the loss of both anodal capture and cathodal capture, as shown at 1026, then the processor 116 may maintain the current pacing configuration. A loss of both anodal and cathodal capture may indicate that the cathodal capture threshold is lower than the anodal capture threshold. Thus, there may be no need to repeat the cardiac threshold testing. However, if more than two electrodes are available for delivering an electrostimulation therapy, then the IMD 102 may continue to repeat the methods 1000A or 1000B using different combinations of electrodes to identify which electrode of the plurality of electrodes has the lowest capture threshold.

While the methods 1000A and 1000B are described in the context of a step-down capture threshold test, it will be generally understood that the methods 1000A and 1000B may also be carried out using step-up capture threshold testing. During step-up capture threshold testing, the processor 116 may be programmed to identify anodal or cathodal capture rather than the loss of capture.

Figure 11:
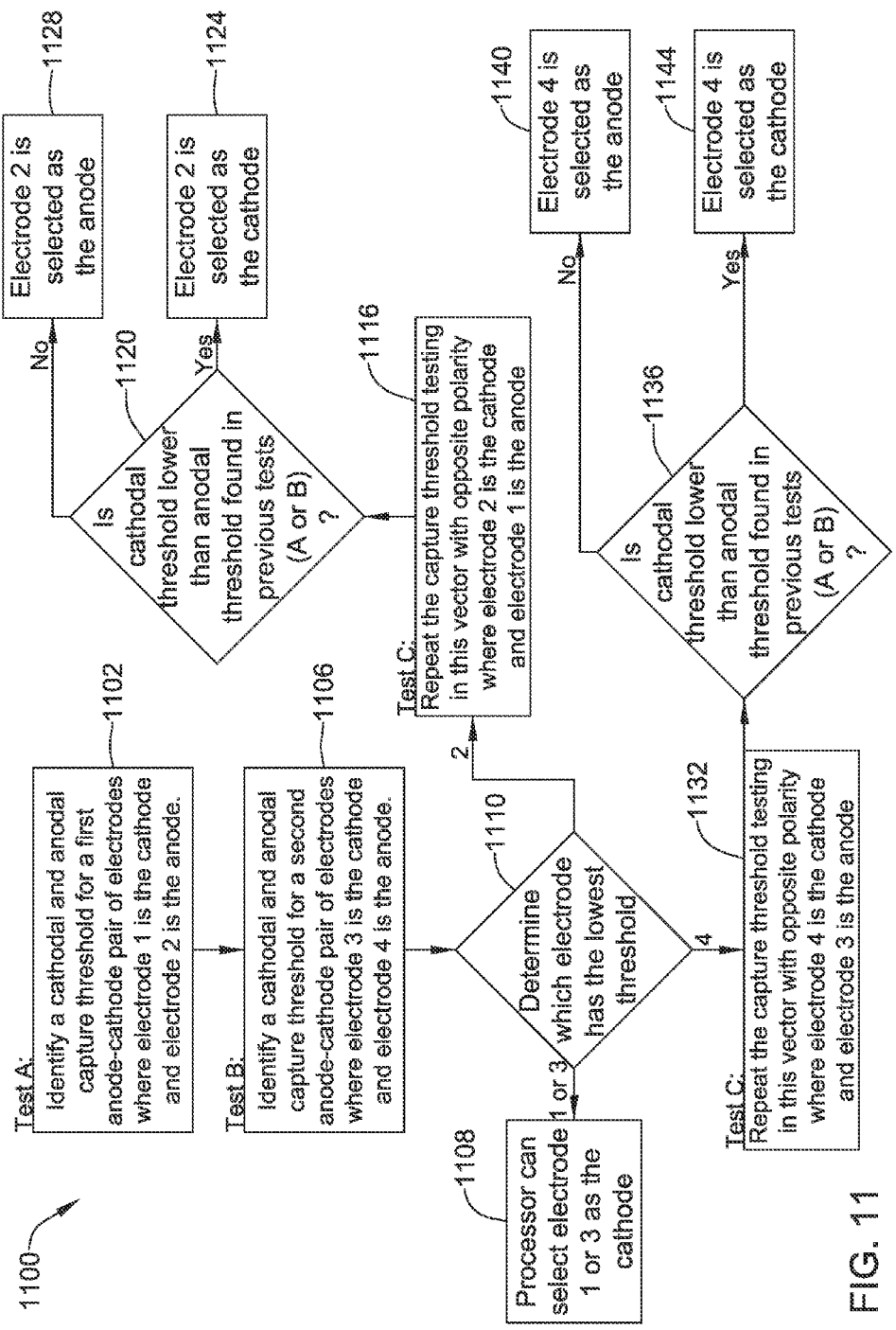
FIG. 11 is a flow chart of another method that may be used to identify an electrode from at least two or more electrodes that has a lower capture threshold for delivering an electrostimulation therapy.

FIG. 11 is a flow chart of another method 1100 that may be used to identify an electrode from at least two or more electrodes that has a lower capture threshold for delivering an electro stimulation therapy. While method 1100 is described as it relates to a quadripolar lead having four electrodes or two anode-cathode pairs of electrodes such as shown, for example, in FIG. 3, this is just one example. It will be generally understood that this method may be used to identify an electrode having the lowest cathodal capture threshold on a lead having any number of electrodes.

For ease of identification, the processor 116 may assign each of the electrodes (e.g. electrodes 302A-302D shown in FIG. 3) on a quadripolar lead (e.g. lead 300) a unique identifier such as a number or letter. For example, each of the four electrodes may be identified by the numbers "1", "2", "3", and "4" and may be located on the lead in that order. In some cases, each of the electrodes may be initially assigned a polarity (positive or negative) such that electrodes "1" and "2" form a first cathode and anode pair of electrodes where electrode "1" is the cathode and electrode "2" is the anode, and electrodes "3" and "4" form a second cathode and anode pair where electrode "3" is the cathode and electrode "4" is the anode.

As shown at 1102, a capture threshold test may be initiated for the first cathode and anode pair of electrodes to identify a cathodal capture threshold and an anodal capture threshold. In addition, as shown at 1106, a second capture threshold test may be initiated for the second cathode and anode pair of electrodes to identify a cathodal capture threshold and an anodal capture threshold for the second pair of electrodes. Next, at 1110, the processor 116 may be programmed to compare the capture thresholds for each of the four electrodes to one another to identify which electrode "1", "2", "3", or "4" has the lowest capture threshold (cathodal or anodal).

Depending upon which electrode is identified as having the lowest capture threshold (cathodal or anodal), the processor 116 may either repeat the capture threshold test or select a cathode based, at least in part, on the electrode having the lowest cathodal capture threshold. In one case, for example, if either electrode "1" or "3" is identified as having the lowest capture threshold (both designated cathodes), then, at 1108, the processor 116 may be programmed to select either electrode "1" or "2" as the cathode for delivering an electrostimulation therapy. However, as shown as 1116, if electrode "2" (designated an anode) is identified as having the lowest capture threshold which, for the purposes of illustration, may be an anodal capture threshold, the processor 116 may be further programmed to re-assign or switch the polarity of electrodes "1" and "2" such that electrode "2" becomes the cathode and electrode "1" becomes the anode, and the capture threshold test may be repeated with the cathode and anode pair of electrodes having the switched polarity. Next, at 1120, the processor 116 may compare the cathodal capture threshold identified for the cathode and anode pair of electrodes having the switched polarity (electrodes "2" and "1") to the anodal capture thresholds identified from the initial capture threshold testing for the first cathode and anode pair of electrodes (electrodes "1" and "2"). If the processor 116 determines that the cathodal capture threshold identified for the cathode and anode pair of electrodes having the switched polarity (electrodes "2" and "1") is lower than the previously identified anodal threshold, then the processor 116 may select electrode "2" as the cathode for the delivery of an electro stimulation therapy, as shown at 1124.

After selecting or identifying a cathode for delivery of an electrostimulation therapy, the processor 116 may be further configured to select the anode. In some cases, the processor 116 may select the electrode having the next lowest capture threshold, but this is not required. In other cases, the processor 116 may select the anode based on criteria which includes a low capture threshold and/or which electrode avoids or minimizes phrenic nerve or unwanted muscle stimulation. Such phrenic nerve stimulation or undesirable muscle stimulation may be detected using a variety of sensors (e.g. physiologic or activity sensors), or in some cases, by input from a user. In some cases, the processor 116 may be configured to prioritize avoiding phrenic nerve stimulation or undesirable muscle stimulation over selecting the electrode having the next lowest capture threshold. This is just one example.

In some instances, the processor 116 may be configured to display the various capture thresholds to a clinician via a remote display such as, for example, the GUI 128 of a remote external interface device 106 as shown in FIG. 1 from which the user may then select the anode for delivering an electrostimulation therapy. The clinician may select the anode according to a variety of criteria including, but not limited to, capture threshold value, phrenic nerve stimulation, muscle stimulation, multi-site pacing desirability, and/or other preferences, and may input their selection via the GUI 128 of the remote external interface device 106 which may then be received and accepted by the processor 116. In some cases, the user may also select which electrode should be the cathode.

In some instances, if the processor 116 determines that the cathodal capture threshold identified for the cathode and anode pair of electrodes having the switched polarity (electrodes "2" and "1") is not lower than the previously identified anodal threshold, then the processor 116 may select electrode "2" as the anode and electrode 1 as the cathode for the delivery of an electro stimulation therapy, as shown at 1128.

The processor 116 may carry out a similar process of selecting the cathode and/or anode to that described above with reference to steps 1116, 1120, 1124 and 1128, if, for example, at 1110, the processor 116 identifies electrode "4" as having the lowest capture threshold. In this example, as described herein, electrode "4" was previously identified as an anode for the initial capture threshold test carried out at 1106. In response to identifying electrode "4" as having the lowest capture threshold, as shown at 1132, the processor 116 may re-assign or switch the polarity of electrodes "3" and "4" such that electrode "4" becomes the cathode and electrode "3" becomes the anode. The capture threshold test may then be repeated with the cathode and anode pair of electrodes having the switched polarity. Next, at 1136, the processor 116 may compare the cathodal capture threshold identified for the cathode and anode pair of electrodes having the switched polarity (electrodes "4" and "3") to the anodal capture thresholds identified from the initial capture threshold testing for the second cathode and anode pair of electrodes (electrodes "3" and "4"). If the processor 116 determines that the cathodal capture threshold identified for the cathode and anode pair of electrodes having the switched polarity (electrodes "4" and "3") is lower than the previously identified anodal threshold, then the processor 116 may select electrode "4" as the cathode for the delivery of an electro stimulation therapy, as shown at 1144.

After selecting or identifying a cathode for delivery of an electro stimulation therapy, the processor 116 may be further configured to select the anode. In some cases, the processor 116 may select the electrode having the next lowest capture threshold, but this is not required. In other cases, the processor 116 may select the anode based on criteria which includes a low capture threshold and/or which electrode avoids or minimizes phrenic nerve or unwanted muscle stimulation. Such phrenic nerve stimulation or undesirable muscle stimulation may be detected using a variety of sensors (e.g. physiologic or activity sensors), or in some cases, by input from a user. In some cases, the processor 116 may be configured to prioritize avoiding phrenic nerve stimulation or undesirable muscle stimulation over selecting the electrode having the next lowest capture threshold. This is just one example.

In some instances, the processor 116 may be configured to display the various capture thresholds to a clinician via a remote display such as, for example, the GUI 128 of a remote external interface device 106 as shown in FIG. 1 from which the user may then select the anode for delivering an electro stimulation therapy. The clinician may select the anode according to a variety of criteria including, but not limited to, capture threshold value, phrenic nerve stimulation, muscle stimulation, multi-site pacing desirability, and/or other preferences, and may input their selection via the GUI 128 of the remote external interface device 106 which may then be received and accepted by the processor 116. In some cases, the user may also select which electrode should be the cathode.

In some instances, if the processor 116 determines that the cathodal capture threshold identified for the cathode and anode pair of electrodes having the switched polarity (electrodes "4" and "3") is not lower than the previously identified anodal threshold, then the processor 116 may select electrode "4" as the anode and electrode "3" as the cathode for the delivery of an electro stimulation therapy, as shown at 1140.

While method 1100 is described in the context of a step-down capture threshold test, it will be generally understood that the method 1100 may also be carried out using step-up capture threshold testing. During step-up capture threshold testing, the processor 116 may be programmed to identify anodal or cathodal capture rather than the loss of capture.

Figure 12:
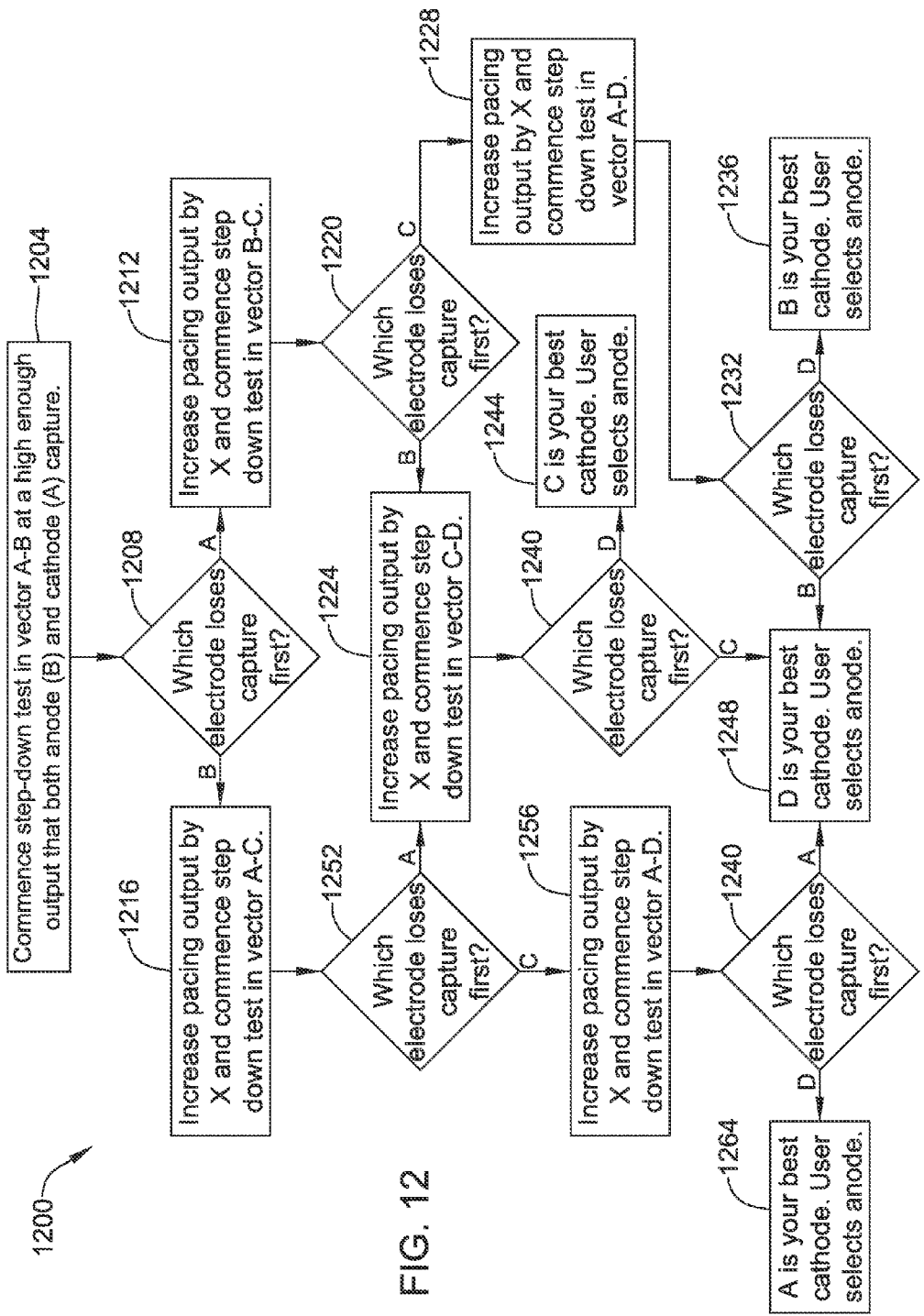
FIG. 12 is a flow chart of yet another method that may be used to identify an electrode from at least two or more electrodes having a low capture threshold for delivering an electrostimulation therapy.

FIG. 12 is a flow chart of yet another method that may be used to identify an electrode from at least two or more electrodes having a low capture threshold for delivering an electro stimulation therapy. Method 1200 may more quickly identify a cathode for delivering stimulation using an elimination process that eliminates potential electrodes based on which electrode loses capture first during a capture threshold test. While method 1200 is described as it relates to a quadripolar lead having four electrodes such as shown, for example, in FIG. 3, this is just one example. It will be generally understood that this method may be used to identify an electrode having a lower cathodal capture threshold on a lead with any number of a plurality of electrodes.

For ease of identification, the processor 116 may assign each of the electrodes (e.g. electrodes 302A-302D shown in FIG. 3) on a quadripolar lead (e.g. lead 300) a unique identifier such as a number or letter. For example, each of the four electrodes may be identified by the letters "A", "B", "C", and "D" and may be located on the lead in that order. In some cases, as shown at 1204, the processor 116 may be programmed to initiate a step-down capture threshold test in a first pacing vector including adjacent electrodes "A" and "B" at a sufficiently high energy level so as to help ensure capture of the both the cathode (electrode "A") and the anode (electrode "B"). The processor 116 may monitor each of the cathode "A" and anode "B" during the threshold test to determine if/when a loss of capture occurs. Upon detecting a loss of capture, at 1208, the processor 116 may be programmed to distinguish between loss of cathodal capture and loss of anodal capture to identify which electrode "A" or "B" loses capture first. The processor 116 may discriminate between loss of anodal capture and loss of cathodal capture using, for example, the methods described herein. If the processor 116 determines that electrode "A" (i.e. the cathode) loses capture first, then, at 1212, the processor 116 may increase the pacing energy output by a predetermined amount and initiate step-down capture threshold testing in a second pacing vector including electrodes "B" and "C", where "B" becomes the cathode and "C" is the anode. Alternatively, if the processor 116 determines that electrode "B" loses capture first (i.e. loss of anodal capture) then, at 1216, the processor 116 may increase the pacing energy output by a predetermined amount and initiate a step-down test using a third pacing vector including electrodes "A" and "C" where "A" remains as the cathode and "C" is the anode.

Referring now to 1212, the processor 116 may monitor each of the cathode "B" and anode "C" to determine when a loss of capture occurs. At 1220, upon detecting a loss of capture, the processor 116 may distinguish between loss of cathodal capture and loss of anodal capture to identify which electrode "B" or "C" loses capture first. If the processor 116 determines that electrode "B" loses capture first (i.e. loss of cathodal capture or anode-only capture), then, at 1224, the processor 116 may increase the pacing energy output by a predetermined amount and initiate step-down capture threshold testing using another pacing vector including electrodes "C" and "D", where "C" is the cathode and "D" is the anode. Alternatively, if the processor 116 determines that electrode "C" loses capture first (i.e. loss of anodal capture or cathode-only capture) then, at 1228, the processor 116 may increase the pacing energy output by a predetermined amount and initiate a step-down test using another pacing vector including electrodes "B" and "D", where "B" remains as the cathode and "C" is the anode.

Continuing the method at 1232, the processor 116 may monitor each of the cathode "B" and anode "D" to determine when a loss of capture occurs. Upon detecting a loss of capture, the processor 116 may distinguish between loss of cathodal capture and loss of anodal capture to identify which electrode "B" or "D" loses capture first. If the processor determines that "D" loses capture first (i.e. loss of anodal capture or cathode-only capture) then, at 1236, the processor 116 may select electrode "B" as the cathode for delivering an electrostimulation therapy since the cathodal capture threshold energy is lower than the anodal capture threshold energy. Conversely, if the processor determines that electrode "B" loses capture first (i.e. loss of cathodal capture or anodal-only capture) then, at 1248, the processor 116 may select electrode "D" as the cathode for delivering an electrostimulation therapy.

Similarly, at 1224, the processor 116 may monitor each of the cathode "C" and anode "D" to determine when a loss of capture occurs. Upon detecting a loss of capture, at 1240, the processor 116 may distinguish between loss of cathodal capture and loss of anodal capture to identify which electrode "C" or "D" loses capture first. If the processor 116 determines that electrode "D" loses capture first (i.e. loss of anodal capture or cathodal-only capture), then, at 1244, the processor 116 may select, in this example, electrode "C" as the cathode for delivering an electrostimulation therapy. Conversely, if the processor 116 determines that electrode "C" loses capture first (i.e. loss of cathodal capture or anodal-only capture), then, at 1248, the processor 116 may select electrode "D" as the cathode for delivering an electrostimulation therapy.

Continuing the method from 1216, the processor 116 may monitor each of the cathode "A" and the anode "C" to determine when a loss of capture occurs. Upon detecting a loss of capture, at 1252, the processor 116 may distinguish between loss of cathodal capture and loss of anodal capture to identify which electrode "A" or "C" loses capture first. If the processor 116 determines that electrode "A" loses capture first (i.e. loss of cathodal capture or anodal-only capture) then, at 1224, the processor 116 may increase the pacing energy output by a predetermined amount and initiate step-down capture threshold testing using another pacing vector including electrodes "C" and "D" where "C" is the cathode and "D" is the anode. The processor 116 may then continue to follow the method as outlined in steps 1240, 1244 and/or 1248, as described above, to identify a cathode from electrodes "C" or "D" for delivering an electrostimulation therapy. Alternatively, if the processor 116 determines that "C" loses capture first (i.e. loss of anodal capture or cathodal-only capture), then, at 1256, the processor 116 may increase the pacing energy output by a predetermined amount and initiate step-down capture threshold testing using another pacing vector including electrodes "A" and "D" where "A" is the cathode and "D" is the anode. At 1260, the processor 116 may monitor each of the cathode "A" and the anode "D" to determine when a loss of capture occurs. Upon detecting a loss of capture, at 1260, the processor 116 may distinguish between loss of cathodal capture and loss of anodal capture to identify which electrode "A" or "D" loses capture first. If the processor 116 determines that electrode "A" loses capture first (i.e. loss of cathodal capture or anodal-only capture), then, at 1248, the processor 116 may be programmed to select "D" as the cathode for delivering an electrostimulation therapy. Conversely, if the processor 116 determines that electrode "D" loses capture first (i.e. loss of anodal capture or cathodal-only capture), then, at 1264, the processor 116 may be programmed to select "A" as the cathode for delivering an electro stimulation therapy.

In some cases, the processor 116 may be further configured to select the anode for delivering an electrostimulation therapy. In some cases, the processor 116 may select the electrode having the next lowest capture threshold as the anode, but this is not required. In other cases, the processor 116 may select the anode based on criteria which includes a low capture threshold and which avoids or minimizes phrenic nerve or unwanted muscle stimulation. Such phrenic nerve stimulation or undesirable muscle stimulation may be detected using a variety of sensors for this purpose (e.g. physiologic or activity sensors), or in some cases, by input from a user. In some cases, the processor 116 may be configured to prioritize avoiding phrenic nerve stimulation or undesirable muscle stimulation over selecting the electrode having the next lowest capture threshold. This is just one example.

In some instances, the processor 116 may be configured to display the various capture thresholds to a clinician via a remote display such as, for example, the GUI 128 of a remote external interface device 106 as shown in FIG. 1 from which the user may then select the anode for delivering an electro stimulation therapy. The clinician may select the anode according to a variety of criteria including, but not limited to, capture threshold value, phrenic nerve stimulation, muscle stimulation, multi-site pacing desirability, and/or other preferences, and may input their selection via the GUI 128 of the remote external interface device 106 which may then be received and accepted by the processor 116. In some cases, the user may also select which electrode should be the cathode.

While method 1200 is described in the context of a step-down capture threshold test, it will be generally understood that the method 1200 may also be carried out using step-up capture threshold testing. During step-up capture threshold testing, the processor 116 may be programmed to identify anodal or cathodal capture rather than the loss of capture.

Figure 13:
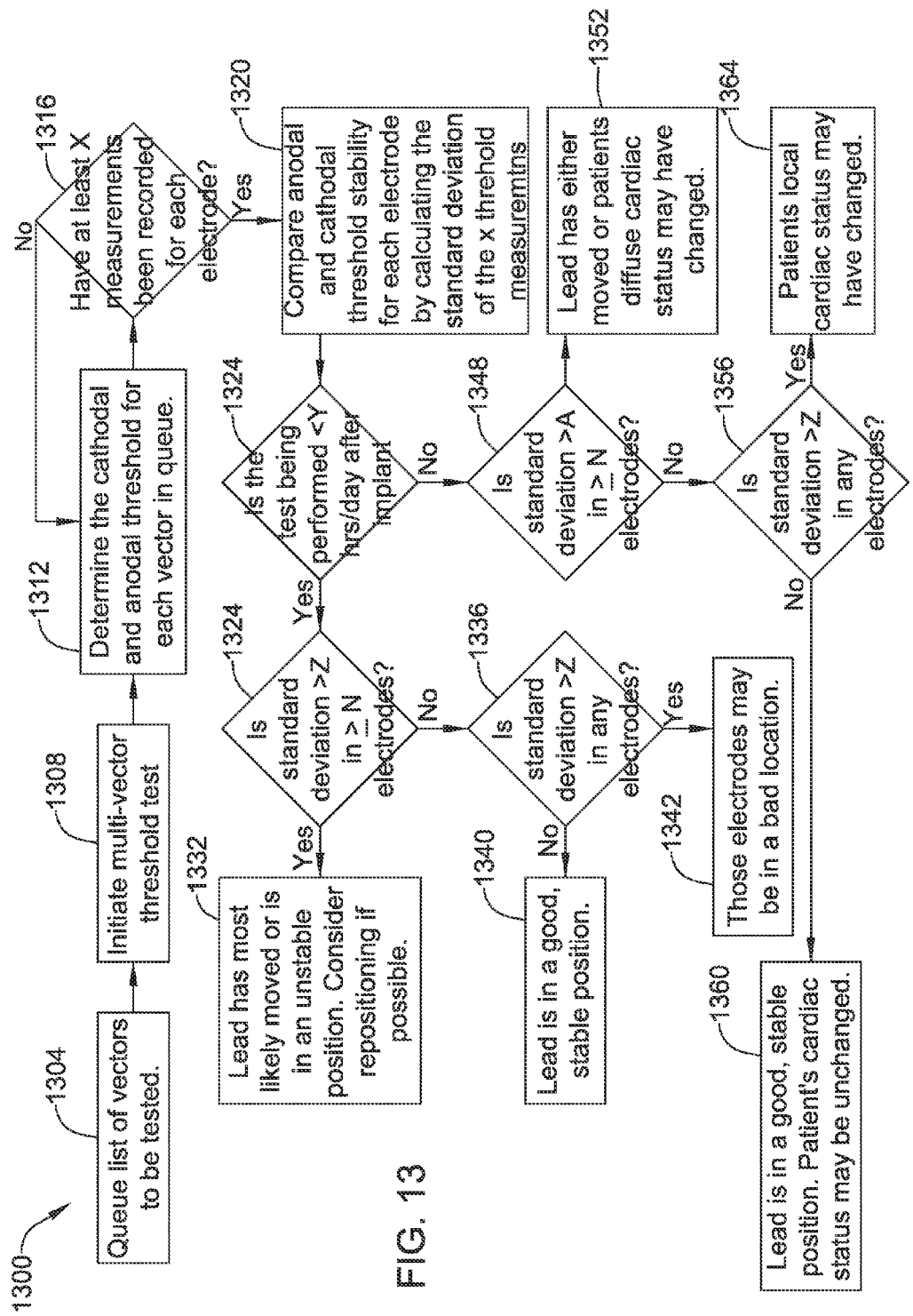
FIG. 13 is a flow chart of a method of determining the stability of a position of a lead implanted within a patient used to deliver an electrostimulation therapy.

FIG. 13 is a flow chart of a method 1300 that may be used in an ambulatory setting to determine the stability of one or more leads implanted within a patient and used to deliver an electrostimulation therapy. Typically, the method 1300 may be executed sometime after implantation of a medical device within a patient such as, for example, an implantable cardiac rhythm or function management device 102. The illustrative method 1300 may use capture threshold testing to determine the anodal and/or cathodal capture thresholds for various electrode vectors of a multi-electrode lead, and based on a standard deviation or other statistical measure of those capture thresholds, determines the stability of the placement and/or function of the electrodes. While the illustrative method 1300 is described as it relates to the placement and testing of a left ventricular lead, it will be generally understood that the illustrative method 1300 may be used to check the stability of placement of one or more electrodes located in other chambers of the heart including the right atrium (RA), the right ventricle (RV), and/or the left atrium (LA).

Turning specifically to FIG. 13, at 1304 the processor 116 may queue a list of pacing vectors for capture threshold testing. In some cases, the various pacing vectors may be part of a pre-determined list of possible pacing vectors that is pre-programmed into the device 102 at the time of manufacture. In other cases, the various pacing vectors selected for testing may be manually selected by a clinician and may be inputted into the processor 116 via the GUI 128 of a remote external interface device 106 which may then be received and accepted by the processor 116. The various pacing vectors listed in the queue may be assigned an order or rank. The order or ranking may be a default ranking pre-programmed into the device 102 at the time of manufacture, or may be selected by a clinician or other user and may be inputted into the processor 116 via the GUI 128 of the remote external interface device 106 which may then be received and accepted by the processor 116. In some cases, the ranking may be based on some preliminary measurements, such as impedance, delay, phrenic stimulation and/or other measurement value(s).

Next, at 1308, multi-vector capture threshold testing may be initiated for each pacing vector in the queue, or a subset of pacing vectors in the queue. In some cases, the multi-vector capture threshold testing maybe initiated after an amount of time has passed after implantation of the device 102 within the patient, or in response to receiving a command initiated by a clinician or other user though the GUI 128 of the remote external interface 106. Using one of the methods as described herein, at 1312 a cathodal capture threshold and an anodal capture threshold (as applicable) may be identified for each pacing vector. The cathodal capture threshold measurement and/or the anodal capture threshold measurement for each pacing vector may be recorded and stored in a memory such as, for example, memory circuit 118. At 1316, steps 1308 and 1312 can be repeated until a predetermined number of cathodal capture threshold measurements and/or anodal capture threshold measure measurements are recorded for each pacing vector. In some cases, at least two cathodal capture threshold measurements and/or three anodal capture threshold measurements may be recorded for each pacing vector. In other cases, the number of predetermined cathodal capture threshold measurements and/or anodal capture threshold measurements recorded for each pacing vector may be greater than two so as to ensure a better statistical distribution, such as four, five, ten, one hundred, or more.

Next, at 1320, the stability of the cathodal capture threshold measurements and/or the stability of the anodal capture threshold measurements may be evaluated and compared. The stability of the cathodal capture threshold measurements and/or the anodal capture threshold measurements may be used to evaluate the position of the lead on which the cathode and/or anode are located. In some cases, the stability of the cathodal capture threshold measurements and/or anodal capture threshold measurements may be based, at least in part, on a standard deviation of each of the cathodal capture threshold measurements and/or anodal capture threshold measurements recorded for each pacing vector.

In some instances, the processor 116 may be programmed to use different criteria for evaluating the stability of the cathodal and/or anodal capture threshold measurements depending upon the amount of time that has passed since implantation of the device 102 within a patient. In some cases, for example, as shown at 1324, the processor 116 may be programmed to determine how much time in hours, days, weeks, months, etc. has passed since implantation of the device 102 within the patient. The processor 116 may include a timer for measuring the length of time from the day of implantation where the day of implantation is time=0 or equivalent. If the processor 116 determines that the capture threshold testing is being performed less than a predetermined number of days or hours after implantation, then, as shown at 1328 the processor 116 may evaluate the standard deviation of each of the cathodal capture threshold measurements and/or anodal capture threshold measurements for each pacing vector using a first predetermined stability threshold value. In some cases, the first predetermined stability threshold value may be selected by a clinician such that it is patient specific. In other cases, the first predetermined stability threshold value may be selected based on clinical data such that it is based on a larger population. In either case, if the processor 116 may determine that the standard deviation of the cathodal capture threshold measurements and/or anodal capture threshold measurements is greater than the first predetermined threshold value for a predetermined number or percentage of the electrodes on the lead, then, at 1332, the processor 116 may be configured to determine that the lead may be in an unstable position. In response to determining that the lead may be in an unstable position, the processor 116 may be programmed to display an alert or transmit a notification to the clinician including an indication that the lead position may be unstable. In some cases, the processor 116 may be programmed to display one or more recommendations to the user regarding one or more possible solutions. In some cases, the alert may be displayed on the GUI 128 of a remote external user interface 106 or may be transmitted to the clinician as a SMS text message or email.

Referring again to 1328, if the processor 116 determines that the standard deviation (or other statistical measure) of the cathodal capture threshold measurements and/or anodal capture threshold measurements is not greater than the first predetermined threshold value for a predetermined number or percentage of the electrodes on the lead, then, as shown at 1336, the processor 116 may be programmed to evaluate whether the standard deviation is greater than the predetermined stability threshold value for any of the electrodes. If no, then, at 1340, the processor 116 may determine that the lead and/or the electrodes are in a stable position for delivering an electrostimulation therapy. If yes, then, at 1342, the processor 116 may determine that the electrodes may be in less than optimal or even an undesirable location for delivering an electrostimulation therapy. In response, the processor 116 may be programmed to display an alert or transmit a notification to the clinician including an indication that the lead position may be sub-optimal. In some cases, the processor 116 may be programmed to display one or more recommendations to the user regarding one or more possible solutions. In some cases, the alert may be displayed on the GUI 128 of a remote external user interface 106 or may be transmitted to the clinician as a SMS text message or email.

Referring back to 1324, if the processor 116 determines that the capture threshold testing is being performed greater than a predetermined number of days or hours after implantation of the IMD, then, as shown at 1348 the processor 116 may evaluate the standard deviation of each of the cathodal capture threshold measurements and/or anodal capture threshold measurements for each pacing vector using a second or different predetermined stability threshold value. In some cases, the second predetermined stability threshold value may be selected by a clinician such that it is patient specific. In other cases, the second predetermined stability threshold value may be selected based on clinical data such that it is based on a larger population. In addition, the second predetermined stability value may be selected or determined such that it is less than the first predetermined stability value.

At 1348, the processor 116 may be configured to determine if the standard deviation of each of the cathodal capture threshold measurements and/or anodal capture threshold measurements is greater than the second predetermined stability threshold value for a predetermined number or percentage of the electrodes on the lead. If yes, then at 1352, the processor 116 may determine that either the lead has moved from its initial position and/or the patient's cardiac status may have changed. In response to determining that the lead may be in an unstable position, the processor 116 may display an alert or transmit a notification to the clinician including an indication that the lead position may have changed and/or the patient's cardiac condition has changed over time. In some cases, the processor 116 may be further programmed to display one or more recommendations to the user regarding one or more possible solutions. In some cases, the alert may be displayed on the GUI 128 of a remote external user interface 106 or may be transmitted to the clinician as a SMS text message or email.

If no, then, at 1356, the processor 116 may determine if the standard deviation of each of the cathodal capture threshold measurements and/or anodal capture threshold measurements is greater than the second predetermined stability threshold value for any of the electrodes. If the processor 116 determines that the standard deviation of any of the cathodal capture threshold measurements and/or anodal capture threshold measurements is not greater than the second predetermined stability threshold value for any of the electrodes then, at 1360, the processor 116 may determine that the lead is in a stable position and/or the patient's condition has not changed over time. Alternatively, if the processor 116 determines that the standard deviation of any of the cathodal capture threshold measurements and/or anodal capture threshold measurements is greater than the second predetermined stability threshold value for all of the electrodes then, at 1364, the processor 116 may determine that the patient's local cardiac status may have changed. For example, a myocardial infarction may have occurred near one or more of the electrodes which may have resulted in an out-of-range standard deviation. In response, the processor 116 may be programmed to display an alert or transmit a notification to the clinician including an indication that the patient's cardiac condition may have changed. In some cases, the processor 116 may be further programmed to display one or more recommendations to the user regarding one or more possible solutions. In some cases, the alert may be displayed on the GUI 128 of a remote external user interface 106 or may be transmitted to the clinician as a SMS text message or email.

Having thus described several illustrative embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The disclo- sure's scope is, of course, defined in the language in which the appended claims are expressed.

What is claimed is:

1. An implantable medical device comprising:
an electrostimulation energy delivery circuit configured to deliver a number of pacing pulses to a subject's heart via an electrode configuration comprising a first electrode and a second electrode;
an evoked response (ER) sensing circuit configured to sense an ER signal of a subject in response to each of the delivered pacing pulses; and
a processor circuit, coupled to the ER sensing circuit and the electrostimulation energy delivery circuit, wherein in an operating mode of the device, the processor circuit is configured to:
cause the electrostimulation energy delivery circuit to deliver a number of pacing pulses using a first polarity with the first electrode as the pacing cathode and the second electrode as the pacing anode;
cause the electrostimulation energy delivery circuit to adjust a pacing energy of the delivered pacing pulses over time, and monitor the ER signal via the ER sensing circuit;
determine, using the ER signal, whether the pacing cathode or the pacing anode has a lower energy pacing capture threshold; and
maintain the first polarity in response to determining the pacing cathode first electrode has the lower pacing capture threshold, and trigger a change to a second polarity in which the first electrode is the pacing anode and the second electrode is the pacing cathode in response to determining the pacing anode second electrode has the lower pacing energy threshold.

2. The implantable medical device of claim 1, wherein the processor circuit is configured to detect a loss of capture at one or both of the first electrode and the second electrode, and change to the second polarity when capture is occurring at the second electrode but not the first electrode.

3. The implantable medical device of claim 1, wherein the processor circuit is configured to initialize the pacing energy to an initial value before causing the electrostimulation energy delivery circuit to adjust the pacing energy of the delivered pacing pulses over time.

4. The implantable medical device of claim 1, wherein the processor circuit is configured to cause the electrostimulation energy delivery circuit to automatically increase the pacing energy of the delivered pacing pulses over time.

5. The implantable medical device of claim 1, wherein after switching the polarity of the first electrode and the second electrode to the second polarity, the processor circuit is further configured to:
cause the electrostimulation energy delivery circuit to deliver a number of pacing pulses using the second polarity of the first electrode and the second electrode and continuing from a pacing energy used for the first polarity;
cause the electrostimulation energy delivery circuit to further adjust the pacing energy of the delivered pacing pulses over time, and monitor the ER signal via the ER sensing circuit until a change is detected that indicates a change in capture at the first electrode and/or the second electrode; and
identify from the evoked response if capture is occurring at the first electrode but not the second electrode, and if so, cause the electrostimulation energy delivery circuit to switch the polarity of the first electrode and the second electrode to the first polarity, and if not, maintain the second polarity of the first electrode and the second electrode.

6. The implantable medical device of claim 1, wherein after switching the polarity of the first electrode and the second electrode to the second polarity, the processor circuit is further configured to:
initialize the pacing energy to an initial value of pacing energy used for the first polarity;
cause the electrostimulation energy delivery circuit to deliver a number of pacing pulses using the second polarity of the first electrode and the second electrode;
cause the electrostimulation energy delivery circuit to adjust the pacing energy of the delivered pacing pulses over time, and monitor the ER signal via the ER sensing circuit until a change is detected that indicates a change in capture at the first electrode and/or the second electrode; and
identify from the evoked response if capture is occurring at the first electrode but not the second electrode, and if so, cause the electrostimulation energy delivery circuit to switch the polarity of the first electrode and the second electrode to the first polarity, and if not, maintain the second polarity of the first electrode and the second electrode.

7. A method of determining a pacing configuration comprising:
delivering a number of pacing pulses to a subject's heart via an electrostimulation energy delivery circuit using a first polarity of a first electrode and a second electrode, wherein the first polarity includes the first electrode as a pacing anode and the second electrode as a pacing cathode;
adjusting a pacing energy of the delivered pacing pulses over time via the electrostimulation energy delivery circuit;
monitoring an evoked response (ER) signal via an ER sensing circuit;
determining, using the ER signal, whether the pacing cathode or the pacing anode has a lower energy pacing capture threshold; and
maintaining the first polarity in response to determining the pacing cathode first electrode has the lower pacing capture threshold, and triggering a change to a second polarity in which the first electrode is the pacing anode and the second electrode is the pacing cathode in response to determining the pacing anode second electrode has the lower pacing energy threshold.

8. The method of claim 7, further comprising:
after switching the polarity of the first electrode and the second electrode, reducing the pacing energy of subsequent pacing pulses until another change in the ER signal is detected.

* * * * *